US011254960B2

(12) United States Patent
Belhocine et al.

(10) Patent No.: US 11,254,960 B2

(45) Date of Patent: Feb. 22, 2022

(54) NUCLEIC ACID AMPLIFICATION

(71) Applicant: Labrador Diagnostics LLC, Wilmington, DE (US)

(72) Inventors: Kamila Belhocine, Palo Alto, CA (US); Pranav Patel, Palo Alto, CA (US); Josephine Lee, Palo Alto, CA (US); Aaron Richardson, Palo Alto, CA (US); Scott Tabakman, Palo Alto, CA (US)

(73) Assignee: Labrador Diagnostics LLC, Wilmington, DE (US)

( * ) Notice: Subject to any disclaimer, the term of this patent is extended or adjusted under 35 U.S.C. 154(b) by 0 days.

(21) Appl. No.: 14/848,220

(22) Filed: Sep. 8, 2015

(65) Prior Publication Data

US 2016/0060673 A1 Mar. 3, 2016

Related U.S. Application Data

(63) Continuation of application No. PCT/US2014/030036, filed on Mar. 15, 2014.

(60) Provisional application No. 61/802,241, filed on Mar. 15, 2013.

(51) Int. Cl.

| | |
|---|---|
| ***C12P 19/34*** | (2006.01) |
| ***C12Q 1/6827*** | (2018.01) |
| ***C12Q 1/6844*** | (2018.01) |

(52) U.S. Cl.

CPC ............ *C12P 19/34* (2013.01); *C12Q 1/6827* (2013.01); *C12Q 1/6844* (2013.01)

(58) Field of Classification Search

CPC ........ C12Q 2521/101; C12Q 2521/501; C12Q 2531/119; C12Q 1/6844; C12P 19/34

See application file for complete search history.

(56) References Cited

U.S. PATENT DOCUMENTS

| | | | |
|---|---|---|---|
| 5,714,320 | A | 2/1998 | Kool |
| 5,834,252 | A | 11/1998 | Stemmer et al. |
| 5,874,260 | A | 2/1999 | Cleuziat et al. |
| 5,928,905 | A | 7/1999 | Stemmer et al. |
| 6,033,881 | A | 3/2000 | Himmler et al. |
| 6,090,552 | A | 7/2000 | Nazarenko et al. |
| 6,194,179 | B1 | 2/2001 | Werner et al. |
| 6,235,502 | B1 | 5/2001 | Weissman et al. |
| 6,620,597 | B1 | 9/2003 | Chen et al. |
| 6,743,605 | B1 | 6/2004 | Rabbani et al. |
| 6,764,821 | B1 | 7/2004 | Rabbani et al. |
| 6,916,634 | B2 | 7/2005 | Kopreski |
| 6,977,148 | B2 | 12/2005 | Dean et al. |
| 6,977,153 | B2 | 12/2005 | Kumar et al. |
| 7,264,930 | B2 | 9/2007 | Rabbani et al. |
| 7,297,485 | B2 | 11/2007 | Bornarth et al. |
| 7,468,245 | B2 | 12/2008 | Rabbani et al. |
| 7,485,417 | B2 | 2/2009 | Rabbani et al. |
| 7,713,691 | B2 | 5/2010 | Rabbani et al. |
| 7,803,579 | B2 | 9/2010 | Mitani et al. |
| 7,955,795 | B2 | 6/2011 | Kumar |
| 7,993,839 | B2 | 8/2011 | Nelson et al. |
| 8,133,989 | B2 | 3/2012 | Rabbani et al. |
| 8,206,902 | B2 | 6/2012 | Mitani et al. |
| 8,236,499 | B2 | 8/2012 | Patel et al. |
| 8,288,092 | B2 | 10/2012 | Rabbani et al. |
| 8,420,323 | B2 | 4/2013 | Miyoshi et al. |
| 8,435,741 | B2 | 5/2013 | Miyoshi et al. |
| 8,445,664 | B2 | 5/2013 | Rabbani et al. |
| 8,486,633 | B2 | 7/2013 | Rabbani et al. |
| 8,709,724 | B2 | 4/2014 | Tabor et al. |
| 2001/0039039 | A1 | 11/2001 | Weissman et al. |
| 2001/0049125 | A1 | 12/2001 | Stemmer et al. |
| 2003/0032016 | A1 | 2/2003 | Barany et al. |
| 2003/0207292 | A1 | 11/2003 | Notomi et al. |
| 2004/0170968 | A1 | 9/2004 | Lizardi |
| 2004/0209272 | A1 | 10/2004 | Ben-Asouli et al. |
| 2005/0037393 | A1 | 2/2005 | Gunderson et al. |
| 2005/0074804 | A1 | 4/2005 | Wang et al. |
| 2005/0084894 | A1 | 4/2005 | Brow et al. |
| 2005/0112631 | A1 | 5/2005 | Piepenburg et al. |
| 2005/0202490 | A1 | 9/2005 | Makarov et al. |
| 2005/0277146 | A1 | 12/2005 | Shigemori et al. |
| 2006/0040300 | A1 | 2/2006 | Dapprich et al. |
| 2006/0188893 | A1 | 8/2006 | Kumar et al. |
| 2006/0194214 | A1 | 8/2006 | Church et al. |
| 2007/0031857 | A1 | 2/2007 | Makarov et al. |
| 2007/0054301 | A1 | 3/2007 | Becker et al. |
| 2007/0128635 | A1 | 6/2007 | Macevicz |
| 2007/0141048 | A1 | 6/2007 | Oleksiewicz et al. |

(Continued)

FOREIGN PATENT DOCUMENTS

| | | |
|---|---|---|
| CA | 1340121 E | 11/1998 |
| CA | 2390309 A1 | 5/2001 |

(Continued)

OTHER PUBLICATIONS

Dietrich et al., "Gene assembly based on blunt-ended double-stranded DNA-modules," Biotechnology Techniques, January, vol. 12, No. 1, pp. 49-54. (Year: 1998).*

Notice of Allowance dated Sep. 7, 2016 for U.S. Appl. No. 14/546,998.

Office Action dated Sep. 27, 2016 for U.S. Appl. No. 14/214,850.

White et al. Concatemer Chain Reaction: a Taq DNA Polymerase-Mediated Mechanism for Generating Long Tandemly Repetitive DNA Sequences. Analytical Biochemistry, Academic Press Inc, New York, vol. 199, No. 2, Dec. 1, 1991, pp. 184-190.

(Continued)

*Primary Examiner* — Young J Kim

(57) ABSTRACT

Methods and compositions for the amplification of nucleic acids are disclosed. Amplification methods provided herein may be performed under isothermal conditions. Methods and compositions may include reagents such as nucleic acid polymerases, ligases, and primers.

13 Claims, 6 Drawing Sheets

Specification includes a Sequence Listing.

(56) References Cited

U.S. PATENT DOCUMENTS

| | | | |
|---|---|---|---|
| 2008/0227160 | A1 | 9/2008 | Kool |
| 2008/0305535 | A1 | 12/2008 | Auerbach |
| 2009/0098566 | A1 | 4/2009 | Notomi et al. |
| 2009/0098612 | A1 | 4/2009 | Rhee et al. |
| 2009/0143235 | A1 | 6/2009 | Drmanac et al. |
| 2009/0155856 | A1 | 6/2009 | Miyoshi et al. |
| 2009/0233277 | A1 | 9/2009 | Murakami |
| 2010/0029505 | A1 | 2/2010 | Payan et al. |
| 2010/0075384 | A1 | 3/2010 | Kong et al. |
| 2010/0151471 | A1 | 6/2010 | Faham et al. |
| 2011/0123991 | A1 | 5/2011 | Hoser |
| 2012/0315642 | A1 | 12/2012 | Kankia |
| 2012/0322666 | A1 | 12/2012 | Pham et al. |
| 2013/0005585 | A1 | 1/2013 | Anderson et al. |
| 2013/0040344 | A1 | 2/2013 | Ju |
| 2013/0296535 | A1 | 11/2013 | Church et al. |
| 2013/0330722 | A1 | 12/2013 | Miller |
| 2014/0113839 | A1 | 4/2014 | Wu et al. |
| 2014/0295439 | A1 | 10/2014 | Patel |
| 2014/0295440 | A1 | 10/2014 | Belhocine et al. |
| 2014/0295447 | A1 | 10/2014 | Hayashizaki et al. |
| 2014/0295498 | A1 | 10/2014 | Turner et al. |
| 2014/0302504 | A1 | 10/2014 | Belhocine et al. |
| 2014/0329282 | A1 | 11/2014 | Nelson et al. |
| 2014/0364764 | A1 | 12/2014 | Jung et al. |
| 2015/0140567 | A1 | 5/2015 | Belhocine et al. |
| 2016/0032357 | A1 | 2/2016 | Barany et al. |
| 2016/0060674 | A1 | 3/2016 | Patel |
| 2016/0068895 | A1 | 3/2016 | Belhocine et al. |
| 2016/0076069 | A1 | 3/2016 | Belhocine et al. |
| 2016/0281155 | A1 | 9/2016 | Patel |
| 2016/0376647 | A1 | 12/2016 | Travers et al. |

FOREIGN PATENT DOCUMENTS

| | | | |
|---|---|---|---|
| CN | 101906488 | A | 12/2010 |
| EP | 0833942 | B1 | 8/2000 |
| EP | 2048248 | A1 | 4/2009 |
| EP | 0971039 | B1 | 3/2011 |
| EP | 2692870 | A1 | 2/2014 |
| GB | 2332516 | A | 6/1999 |
| JP | 04131099 | | 5/1992 |
| JP | 07016094 | | 1/1995 |
| JP | 07067646 | A2 | 3/1995 |
| WO | 1992001813 | A1 | 2/1992 |
| WO | 1994003624 | A1 | 2/1994 |
| WO | 1996001327 | A1 | 1/1996 |
| WO | 1997004131 | A1 | 2/1997 |
| WO | 2000079009 | A2 | 12/2000 |
| WO | 02068683 | A2 | 9/2002 |
| WO | 03072805 | A2 | 9/2003 |
| WO | 2004061119 | A2 | 7/2004 |
| WO | 2004070053 | A2 | 8/2004 |
| WO | 2005030983 | A2 | 4/2005 |
| WO | 2005059178 | A1 | 6/2005 |
| WO | 2006095169 | A1 | 9/2006 |
| WO | 2006119066 | A2 | 11/2006 |
| WO | 2007087262 | A2 | 8/2007 |
| WO | 2008012529 | A1 | 1/2008 |
| WO | 2008032058 | A2 | 3/2008 |
| WO | 2009120372 | A2 | 10/2009 |
| WO | 2009120374 | A2 | 10/2009 |
| WO | 2010117817 | A2 | 10/2010 |
| WO | 2012012037 | A1 | 1/2012 |
| WO | 2012017210 | A1 | 2/2012 |
| WO | 2013003585 | A2 | 1/2013 |
| WO | 2013035875 | A1 | 3/2013 |
| WO | 2013036685 | A1 | 3/2013 |
| WO | 2014025337 | A1 | 2/2014 |

OTHER PUBLICATIONS

Fire et al. Rolling replication of short DNA circles, Proceedings of the National Academy of Sciences, National Academy of Sciences, US, vol. 92, No. 10, May 1995.

Horton et al. Engineering hybrid genes without the use of restriction enzymes: gene splicing byoverlap extension. Gene, Elsevier, Amsterdam, NL, vol. 77, No. 1, Apr. 15, 1989, pp. 61-68.

Liu et al. Rolling Circle DNA Synthesis: Small Circular Oligonucleotides as Efficient Templates for DNA Polymerases, Journal of the American Chemical Society, American Chemical Society, US, vol. 118, No. 7, 1996.

Lizardi et al. Mutation detection and single-molecule counting using isothermal rolling-circle amplification, Nature Genetics, Nature Publishing Group, New York, US, vol. 19, No. 3, Jul. 1998.

Marciniak et al. Coupled rolling circle amplification loop-mediated amplification for rapid detection of short DNA sequences, Biotechniques, 2008, 45:275-280.

Office Action dated Nov. 25, 2016 for U.S. Appl. No. 14/214,854.

Sharbati-Tehrani et al. Concatameric cloning of porcine microRNA molecules after assembly PCR. Biochemical and Biophysical Research Communications, Elsevier, Amsterdam, NL, vol. 375, No. 3, Oct. 24, 2008, pp. 484-489.

Notice of Allowance dated Mar. 4, 2016 for U.S. Appl. No. 14/214,848.

Office Action dated Jul. 6, 2016 for U.S. Appl. No. 14/546,998.

Office Action dated Sep. 15, 2017 for U.S. Appl. No. 14/214,854.

Prithiviraj et al. Rapid detection of microbial DNA by a novel isothermal genome exponential amplification reaction (GEAR) assay, Biochemical and Biophysical Research Communications, vol. 420, No. 4, Mar. 12, 2012, pp. 738-742.

Xu et al. Cross Priming Amplification: Mechanism and Optimization for Isothermal DNA Amplification, Scientific Reports, vol. 2, Feb. 2, 2012.

Dean et al. Rapid Amplification of Plasmid and Phase DNA Using Phi29 DNA Polymerase and Multiply-Primed Rolling Circle Amplification, Genome Research, 2001, vol. 11, pp. 1095-1099.

G.J Hafner, et al. Isothermal Amplification and Multimerization of DNA by Bst DNA Polymerase. BioTechniques 30:852-867; Apr. 2001.

International Search Report and Written Opinion dated Aug. 14, 2014 for Application No. PCT/US2014/030028.

International Search Report and Written Opinion dated Aug. 14, 2014 for Application No. PCT/US2014/030036.

International Search Report and Written Opinion dated Sep. 18, 2014 for PCT/US2014/030034.

Lee et al. Versatile PCR-mediated insertion or deletion mutagenesis, Biotechniques, 2004, vol. 36, No. 3, pp. 398-400.

Merriam-Webster, definition of "analogous", available at http://www.merriam-webster.com/dictionary/analogous, accessed May 18, 2015.

Merriam-Webster, definition of "partner", available at http://www.merriam-webster.com/dictionary/partner, accessed May 18, 2015.

Merriam-Webster, definition of "portion", available at http://www.merriam-webster.com/dictionary/portion, accessed May 18, 2015.

Merriam-Webster, definition of "represent", available at http://www.merriam-webster.com/dictionary/represent, accessed May 18, 2015.

Notomi et al. Loop-medicated isothermal amplification of DNA, Nucleic Acids Res. Jun. 15, 2000;28(12):E63.

Office Action dated Oct. 26, 2015 for U.S. Appl. No. 14/546,998.

Office Action dated Oct. 30, 2015 for U.S. Appl. No. 14/214,848.

Office Action dated Jun. 8, 2015 for U.S. Appl. No. 14/546,998.

Ohshima K and Wells RD. Hairpin formation during DNA synthesis primer realignment in vitro in triplet repeat sequences from human hereditary disease genes. Journal of Biological Chemistry 272:16798-16806; Jul. 1997.

Patel R et al. Formation of chimeric DNA primer extension products by template switching onto an annealed downstream oligonucleotide. PNAS 93:2969-2974; Apr. 1996.

Wang et al. Rolling circle amplification-mediated hairpin RNA (RMHR) library construction in plants, Nucleic Acids Research, 2008, vol. 36, No. 22, e149, pp. 1-8.

Wilton SD et al. Snapback SSCP analysis: Engineered conformation changes for the rapid typing of known mutations. Human Mutation 11:252-258; Mar. 1998.

Written Opinion and International Search Report dated Dec. 25, 2014 for PCT/US2014/056151.

(56) References Cited

OTHER PUBLICATIONS

Ashford. Path using TwistDx's Amplification Tech in Minimally Instrumented HIV Test for Infants, GenomeWeb, Aug. 25, 2011.
Euler et al. Recombinase polymerase amplification assay for rapid detection of Rift Valley fever virus. J Ciin Virol. Aug. 2012;54(4):308-12. Epub Jun. 9, 2012.
Office Action dated May 11, 2016 for U.S. Appl. No. 14/546,998.
Rohrman et al. A Paper and Plastic Device for Performing Recombinase Polymerase Amplification of HIV DNA. Lab Chip, Sep. 7, 2012;12(17):3082-8. Epub Jun. 26, 2012.

* cited by examiner

NUCLEIC ACID AMPLIFICATION

BACKGROUND

There is an increasing need for methods and reagents for the amplification of nucleic acids. Generation of multiple copies of a particular nucleic acid is often necessary or helpful in order for the nucleic acid to be used for a given application. For example, in order to analyze the nucleotide sequence of a nucleic acid of interest, frequently, the nucleic acid is replicated to increase its copy number before the sequence is analyzed. In another example, in order to determine the presence or absence of a particular nucleic acid in a sample, a sample may be treated under conditions such that if the particular nucleic acid is present in the sample, it may be amplified. In another example, a nucleic acid for use as a probe may be copied repeatedly to generate a large number of nucleic acids containing the same sequence as the original nucleic acid template, thereby generating many copies of the nucleic acid which may be used as a probe.

A variety of methods for the amplification of nucleic acids are known. For example, polymerase chain reaction ("PCR") (see, e.g. U.S. Pat. No. 4,683,202) is a popular method for the amplification of nucleic acids. To successfully perform a PCR reaction, the reaction must be performed at multiple different temperatures, which are repeated for multiple cycles. This requires hardware or other mechanisms for repeatedly changing the temperature of the PCR reaction. Another method for amplification of nucleic acids is referred to as loop-mediated isothermal amplification ("LAMP") (see, e.g. U.S. Pat. No. 6,410,278). LAMP reactions may be performed isothermally, but typically involve the use of four different primers which recognize a total of six distinct sequences on the target nucleic acid.

To facilitate the generation of amplified nucleic acids for the many and growing number of applications which use amplified nucleic acids, new methods and reagents for the amplification of nucleic acids are desired.

INCORPORATION BY REFERENCE

All publications, patents, and patent applications mentioned in this specification are herein incorporated by reference to the same extent as if each individual publication, patent, or patent application was specifically and individually indicated to be incorporated by reference. However, in the event of a conflict between the content of the present express disclosure and the content of a document incorporated by reference herein, the content of the present express disclosure controls.

SUMMARY

Provided herein are methods and compositions relating to the amplification of nucleic acids and the generation of concatemers.

In some embodiments, a method is provided herein for amplifying a double stranded nucleic acid template, comprising, (A) preparing a reaction mixture comprising: (i) a double-stranded nucleic acid comprising at least one copy of the double-stranded nucleic acid template, wherein the double-stranded nucleic acid comprises a first strand and a second strand, (ii) an isolated nucleic acid polymerase, (iii) an isolated nucleic acid ligase, (iv) a first primer, wherein the first primer is complementary to the first strand of the double-stranded nucleic acid template, (v) a second primer, wherein the second primer is complementary to the second strand of the double-stranded nucleic acid template, and (B) incubating the reaction mixture at a temperature of no greater than 70 C for at least 5 minutes, wherein a plurality of concatemers comprising at least two copies of the double-stranded nucleic acid template are generated, and the double-stranded nucleic acid template is amplified at least 100-fold within 60 minutes of initiation of the method.

In some embodiments, a method is provided herein for amplifying a double-stranded nucleic acid template, wherein a reaction mixture is prepared such that a double-stranded nucleic acid comprising two or more copies of the double-stranded nucleic acid template may undergo a primer-based replication process, a cross-over strand-based replication process, or an end-to-end ligation process. In some embodiments, the reaction mixture is prepared and incubated such that all three processes simultaneously occur in the reaction mixture.

In some embodiments, a method is provided herein for amplifying a double-stranded nucleic acid template, wherein a reaction mixture is prepared such that a double-stranded nucleic acid comprising a single copy of the double-stranded nucleic acid template may optionally undergo any one or both of a primer-based replication process or an end-to-end ligation process. In some embodiments, a method is provided herein for amplifying a double-stranded nucleic acid template, wherein a reaction mixture is prepared such that a double-stranded nucleic acid comprising two or more copies of the double-stranded nucleic acid template may optionally undergo any one, two, or three of a primer-based replication process, a cross-over strand-based replication process, or an end-to-end ligation process. In some embodiments, a method is provided herein for amplifying a double-stranded nucleic acid template, wherein a reaction mixture is prepared such that a double-stranded nucleic acid comprising a single copy of the double-stranded nucleic acid template may optionally undergo any one or both of a primer-based replication process or an end-to-end ligation process and such that a double-stranded nucleic acid comprising two or more copies of the double-stranded nucleic acid template may optionally undergo any one, two, or three of a primer-based replication process, a cross-over strand-based replication process, or an end-to-end ligation process.

In embodiments, provided herein is a method of replicating a double stranded nucleic acid template, the method comprising, incubating in a reaction mixture a first primer, a DNA polymerase, a nucleic acid ligase, a first copy, second copy, and third copy of a single template linear double-stranded nucleic acid, and a first copy and second copy of a multiple template linear double-stranded nucleic acid for at least 5 minutes at a temperature of no greater than 80 C, wherein: the DNA polymerase has strand-displacement activity, the nucleic acid ligase has activity on blunt-ends of double-stranded nucleic acids, each copy of the single template linear double-stranded nucleic acids contains a single copy of the double stranded nucleic acid template, each copy of the single template linear double-stranded nucleic acid and multiple template linear double-stranded nucleic acid comprises: i) a first strand and a second strand, each strand comprising a 5' end and a 3' end, and ii) a first end and a second end, the first end comprising the 5' end of the first strand and the 3' end of the second strand, and the second end comprising the 5' end of the second strand and the 3' end of the first strand, and during the incubation of the reaction mixture, i) the first primer anneals to the first strand of the first copy of the single template linear double-stranded nucleic acid and serves as a primer for the generation of an extension product of the first primer, wherein the extension product of the first primer is complementary to the first stand of the double stranded nucleic acid; ii) the second end of the second copy of the single template linear double-stranded nucleic acid is ligated to the first end of the third copy of the single template linear double-stranded nucleic acid; and iii) a cross-over structure comprising the second strand of the first copy of the multiple template linear double-stranded nucleic acid annealed the first strand of the second copy of the multiple template linear double-stranded nucleic acid is formed, wherein the 3' end of the second strand of the first copy of the multiple template linear double-stranded nucleic acid serves as a primer for the generation of a new concatamer second strand, and wherein the 3' end of the first strand of the second copy of the multiple template linear double-stranded nucleic acid serves as a primer for the generation of a new concatemer first strand.

In embodiments, provided herein is a method for amplifying a double stranded nucleic acid template, the method comprising, incubating a double-stranded nucleic acid comprising the double-stranded nucleic acid template in a reaction mixture, the reaction mixture comprising an isolated nucleic acid polymerase having strand displacement activity, an isolated nucleic acid ligase, a first primer, and a second primer, wherein: the double-stranded nucleic acid template comprises a first strand and a second strand; the first primer is complementary to the first strand of the double-stranded nucleic acid template, wherein the second primer is complementary to the second strand of the double-stranded nucleic acid template, the reaction mixture is maintained at a temperature of no greater than 70 C during the incubation, and upon incubation of the double-stranded nucleic acid comprising the double-stranded nucleic acid template in a reaction mixture, a plurality of concatemers comprising at least two copies of the double-stranded nucleic acid template are generated, and the double-stranded nucleic acid template is amplified at least 100-fold within 60 minutes of initiation of the method.

In embodiments, provided herein is a vessel comprising in fluid communication therein: a first primer, a second primer, a DNA polymerase, a nucleic acid ligase, and a plurality of concatemers, wherein: the DNA polymerase has strand-displacement activity, the nucleic acid ligase has activity on blunt-ends of double-stranded nucleic acids, the first primer is complementary to a first portion of a polynucleotide template, the second primer is complementary to a partner nucleotide sequence, wherein the partner nucleotide sequence is complementary to a second portion of the polynucleotide template, the concatemers are double-stranded molecules, each comprising at least two copies of a double-stranded nucleic acid template, and the plurality of concatemers comprise a first concatemer, second concatemer, and third concatemer, and each of the first concatemer, second concatemer, and third concatemer comprise at least 5 copies of the double-stranded nucleic acid template.

In embodiments, in a method, reaction mixture, vessel, or kit provided herein involving a plurality of concatemers, the plurality of comprise a first concatemer, second concatemer, and third concatemer. In embodiments, each of the first concatemer, second concatemer, and third concatemer each comprise at least 3, 4, 5, 6, 7, 8, 9, 10, 15, 20, or 50 copies of the double-stranded nucleic acid template.

In embodiments, in a concatemer comprising at least 3, 4, 5, 6, 7, 8, 9, 10, 15, 20, or 50 copies of a double-stranded nucleic acid template, each of the at least 3, 4, 5, 6, 7, 8, 9, 10, 15, 20, or 50 copies of the double-stranded nucleic acid template is directly linked in the concatemer in series.

In some embodiments, in methods provided herein involving the amplification of nucleic acid templates or the generation of concatemers, a plurality of concatemers comprising at least 2, 3, 4, 5, 6, 7, 8, 9, 10, 11, 12, 13, 14, 15, 20, 25, 30, 50, 100, 500, or 1000 copies of a nucleic acid template are generated. In some embodiments, in compositions or methods provided herein involving a plurality of concatemers, the plurality of concatemers may comprise a first concatemer, second concatemer, and third concatemer. In embodiments, each of the first concatemer, second concatemer, and third concatemer may contain at least 3, 4, 5, 6, 7, 8, 9, 10, 11, 12, 13, 14, 15, 20, 25, 30, 50, 100, 500, or 1000 copies of a nucleic acid template.

In embodiments, a reaction mixture, vessel, or kit provided herein comprises a reverse transcriptase.

In embodiments, in a method, reaction mixture, vessel, or kit provided herein involving a double-stranded nucleic acid template, the double-stranded nucleic acid is generated from a single-stranded RNA molecule.

In some embodiments, provided herein is a vessel, comprising in fluid communication therein: (A) an isolated nucleic acid polymerase, (B) an isolated nucleic acid ligase, (C) a nucleic acid template comprising at least a first strand, (D) a first primer, wherein the first primer is complementary to a first strand of a double-stranded nucleic acid template, and (E) a second primer, wherein the second primer is complementary to a second strand of the double-stranded nucleic acid template.

In some embodiments, provided herein is a kit for detecting a target nucleic acid of interest comprising at least a first strand, the kit comprising two or more fluidically isolated containers, the containers collectively comprising: (A) an isolated nucleic acid polymerase, (B) an isolated nucleic acid ligase, (C) a first primer, wherein the first primer is complementary to the first strand of the target nucleic acid of interest, (E) a second primer, wherein the second primer is complementary to a sequence complementary the first strand of the target nucleic acid of interest. In some embodiments, the kit comprises the target nucleic acid of interest.

In some embodiments, a target nucleic acid provided herein is a double-stranded nucleic acid template.

In some embodiments, in a method, kit, or vessel provided herein comprising a first and second primer, the primers each comprise at least 4, 5, 6, 7, 8, 9, 10, 11, 12, 13, 14, 15, 16, 17, 18, 19, or 20 nucleotides. In some embodiments, in a method, kit, or vessel provided herein comprising a first and second primer, the primers each comprise no more than 4, 5, 6, 7, 8, 9, 10, 11, 12, 13, 14, 15, 16, 17, 18, 19, 20, 30, 40, or 50 nucleotides.

In some embodiments, all of the processes of a method provided herein are performed at a temperature of no greater than 85, 80, 75, 70, 65, 60, 65, 60, 55, 50, 45, 40, 35, 30, 25, 20, 15, or 10 C. In some embodiments, some of the processes of a method provided herein are performed at a temperature of no greater than 85, 80, 75, 70, 65, 60, 65, 60, 55, 50, 45, 40, 35, 30, 25, 20, 15, or 10 C.

In some embodiments, two or more processes of a method provided herein are performed simultaneously in the same reaction. In some embodiments, all of the processes of a method provided herein are performed simultaneously in the same reaction.

In some embodiments, in a method provided herein, a nucleic acid template is amplified at least 10, 100, 1000, 10,000, 100,000, or 1,000,000-fold within 5, 10, 15, 20, 30, 40, 50, 60, 70, 80, 90, 120, or 180 minutes of initiation of the method.

In some embodiments, a kit provided herein comprises a nucleic acid having the nucleotide sequence of the target nucleic acid of interest.

In some embodiments, a reaction mixture, vessel or kit provided herein comprises a nucleic acid dye.

In some embodiments, in a vessel or kit provided herein comprising an isolated nucleic acid polymerase, the isolated nucleic acid polymerase is a DNA polymerase. In some embodiments, in a vessel or kit provided herein comprising an isolated nucleic acid polymerase, the isolated nucleic acid polymerase is a reverse transcriptase. In some embodiments, in a vessel or kit provided herein comprising an isolated nucleic acid polymerase, the vessel or kit comprises both a DNA polymerase and a reverse transcriptase.

In some embodiments, in a method, vessel, or kit provided herein comprising a nucleic acid polymerase, the nucleic acid polymerase has strand displacement activity.

In embodiments, a reaction mixture, vessel, or kit provided herein comprises a nucleic acid polymerase. In embodiments, a nucleic acid polymerase is a DNA polymerase having strand-displacement activity. In embodiments, a nucleic acid polymerase is an RNA polymerase. In embodiments, a nucleic acid polymerase is a reverse transcriptase. In embodiments, a reaction mixture, vessel, or kit comprises more than one kind of nucleic acid polymerase, such as both a DNA polymerase having strand displacement activity and a reverse transcriptase. In embodiments, a reaction mixture, vessel, or kit provided herein comprises nucleotides and buffer.

In embodiments, in a method, reaction mixture, vessel, or kit provided herein involving a polynucleotide template, the polynucleotide template is a single-stranded molecule. In embodiments, in a method, reaction mixture, vessel, or kit provided herein involving a polynucleotide template, the polynucleotide template comprises one strand of a double-stranded nucleic acid template. In embodiments, in a method, reaction mixture, vessel, or kit provided herein involving a polynucleotide template, the polynucleotide template is a DNA or RNA molecule.

In embodiments, in a method, reaction mixture, vessel, or kit provided herein involving a nucleic acid template, the nucleic acid template is an RNA or DNA molecule. In embodiments, a nucleic acid template may be a single-stranded or double-stranded molecule.

In embodiments, in a method provided herein involving incubation of a reaction mixture, during the incubation of the reaction mixture, the temperature of the reaction mixture does not exceed 90, 85, 80, 75, 70, 65, 60, 55, 50, 45, 40, 37, 35, 30, 25, or 20 C. In embodiments, in a method provided herein, all steps of the method are performed at a temperature of no greater than 90, 85, 80, 75, 70, 65, 60, 55, 50, 45, 40, 37, 35, 30, 25, or 20 C. In embodiments, a reaction mixture, vessel, or kit provided herein is maintained at a temperature of no greater than 90, 85, 80, 75, 70, 65, 60, 55, 50, 45, 40, 37, 35, 30, 25, or 20 C. In embodiments, a method provided herein is performed without thermocycling.

In embodiments, a reaction mixture, vessel, or kit provided herein does not contain a recombinase enzyme.

In embodiments, in a method, reaction mixture, vessel, or kit provided herein may contain or involve multiple copies of a primer. The multiple copies may be, for example, at least 5, 10, 15, 20, 50, 100, 500, 1000, 10,000, 100,000, or 1,000,000 copies of the primer.

In embodiments, a reaction mixture or vessel provided herein may comprise at least a portion of a biological sample from a subject. The biological sample may be, for example, saliva, blood, urine, a cheek swab, or a nasal swab. The subject may be a human.

In some embodiments, two or more steps of a method provided herein are performed simultaneously in the same reaction mixture. In some embodiments, all of the steps of a method provided herein are performed simultaneously in the same reaction mixture.

In some embodiments, in a method provided herein, a nucleic acid template is amplified at least 10, 100, 1000, 10,000, 100,000, or 1,000,000-fold within 5, 10, 15, 20, 30, 40, 50, 60, 70, 80, 90, 120, or 180 minutes of initiation of the method. In some embodiments, in a method provided herein, the number of copies of a nucleic acid template in a reaction mixture is increased least 10, 100, 1000, 10,000, 100,000, or 1,000,000-fold within 5, 10, 15, 20, 30, 40, 50, 60, 70, 80, 90, 120, or 180 minutes of initiation of the method.

In embodiments, a nucleic acid template provided herein may be a single-stranded or a double-stranded nucleic acid template.

In embodiments, provided herein is a method of assaying for a pathogen in a sample, the method comprising performing a method as provided herein to amplify nucleic acid from the pathogen. In embodiments, the target nucleic acid used in a composition or method provided herein may be nucleic acid from a pathogen. In embodiments, the first and second primer used in a method provided herein may each contain regions which are complementary to a sequence in the nucleic acid of the pathogen, or which are complementary to a sequence which is complementary to a sequence in the nucleic acid of the pathogen. In embodiments, the nucleic acid of the pathogen may be DNA or RNA. Pathogens may include, without limitation, viruses, bacteria, fungi, and protists. A sample may be from a subject, and may have any of the sample characteristics described elsewhere herein.

In embodiments, a method provided herein for amplification of a nucleic acid may be used for a diagnostic method externally of a human or animal body. For example, a sample may be obtained from a human or animal, and the sample may be assayed for a target nucleic acid of interest with a method provided herein for amplification of nucleic acid.

In embodiments, a method provided herein may include: a) providing one or more reagents for performing a method as provided herein (e.g. one or more of first primer, second primer, nucleic acid template, nucleic acid polymerase, nucleotides, buffer, water, etc.) in a reaction mixture, and b) incubating the reaction mixture at a substantially isothermal temperature, wherein the temperature of the reaction mixture does not diverge from a central temperature by more or less than 20, 15, 10, 9, 8, 7, 6, 5, 4, 3, 2, or 1 degree. Celsius during the incubation. In embodiments, a central temperature may be, for example, 30, 35, 40, 45, 50, 55, 60, 65, 70, 75, or 80 degrees Celsius.

In embodiments, a method provided herein may be performed at a substantially isothermal temperature. In embodiments, a substantially isothermal temperature may be any of 30, 35, 40, 45, 50, 55, 60, 65, 70, 75, or 80 degrees Celsius, plus or minus 20, 15, 10, 9, 8, 7, 6, 5, 4, 3, 2, or 1 degree Celsius.

In embodiments, a method provided herein may be performed at one or more temperatures, none or which exceed 90, 85, 80, 75, 70, 65, 60, 55, 50, 45, 40, 35, 30, or 25 degrees Celsius.

In compositions and methods provided herein involving a nucleic acid polymerase, in embodiments, the nucleic acid polymerase has 3' to 5' exonuclease activity.

References herein to generating a copy of or amplifying a polynucleotide template or nucleic acid template include generating a copy which contains the sequence of the polynucleotide template/nucleic acid template, as well as generating a copy which contains an analogous sequence of the polynucleotide template/nucleic acid template, unless the context clearly dictates otherwise. For instance, if a polynucleotide template is RNA, generating a copy of the template can include generating a copy which is a DNA molecule which contains the DNA version of the RNA sequence of the polynucleotide template (i.e. in the DNA sequence, contains Ts instead of Us).

In some embodiments, a method provided herein comprises treating one or more of the reaction components or steps of the method with a nucleic acid dye.

In some embodiments, methods provided herein may include generating a linear double-stranded nucleic acid template for use in a process provided herein from a single-strand target molecule. A single-strand target molecule may be DNA or RNA (e.g. mRNA).

In some embodiments, a method provided herein comprises measuring a fluorescent signal from an assay comprising the method.

In some embodiments, a nucleic acid ligase may be included with a method or composition provided herein. In some embodiments, a nucleic acid template may be amplified more rapidly with a method provided herein when a ligase is included in a reaction mixture for a method provided herein, as compared to if a nucleic acid ligase is not included in the reaction.

In some embodiments, amplification methods provided herein may be performed without thermocycling.

In some embodiments, amplification methods provided herein may be performed at a constant temperature. In some embodiments, amplification methods provided herein may be performed within a temperature range of extending no more than 1, 2, 3, 4, 5, 6, 7, 8, 9, 10, 15, 20, 25, or 30 degrees C. above or below a set temperature of 10, 15, 20, 25, 30, 35, 40, 45, 50, 55, 60, 65, 70, 75, or 80 C.

In some embodiments, amplification methods provided herein may comprise incubating a reaction mixture at two, three, four, five or more different temperatures or temperature ranges. In some embodiments, methods provided herein may comprise incubating a reaction mixture at a first temperature, wherein the first temperature is a temperature no greater than 30, 35, 40, 45, 50, 55, 60, 65, 70, or 75 C, and a second temperature, wherein the second temperature is a temperature no greater than 35, 40, 45, 50, 55, 60, 65, 70, 75, or 80 C. In some embodiments, in a method provided herein, a reaction mixture may be maintained at a temperature of no greater than 35, 40, 45, 50, 55, 60, 65, 70, 75, 80, 85, 90, or 95 C during the method.

In some embodiments, methods and compositions provided herein comprise, by volume, at least 10%, 20%, 30%, 40%, 50%, 55%, 60%, 65%, 70%, 75%, 80%, 85%, 90%, 95%, or 98% water. In some embodiments, methods and compositions provided herein comprise, by volume, collectively no more than 1, 2, 3, 4, 5, 10, 15, 20, 25, 30, 35, 40, 45, 50, 60, 70, or 80% glycerol or polyethylene glycol.

In some embodiments, methods provided herein may comprise assaying a sample for a pathogen. In some embodiments, methods provided herein may comprise detecting a pathogen in a sample. In some embodiments, methods provided herein may comprise measuring the quantity of pathogen in a sample. Pathogens may include, for example, bacteria, viruses, protists, and fungi.

In some embodiments, methods provided herein may be performed without the use of a primer which contains self-complementary regions. In some embodiments, methods and compositions provided herein do not comprise a primer which contains self-complementary regions.

In some embodiments, methods and compositions provided herein may be performed or prepared in conjunction with methods and compositions provided in U.S. Provisional Patent Application No. 61/800,606, filed Mar. 15, 2013, which is hereby incorporated by reference in its entirety for all purposes.

Figure 1A:
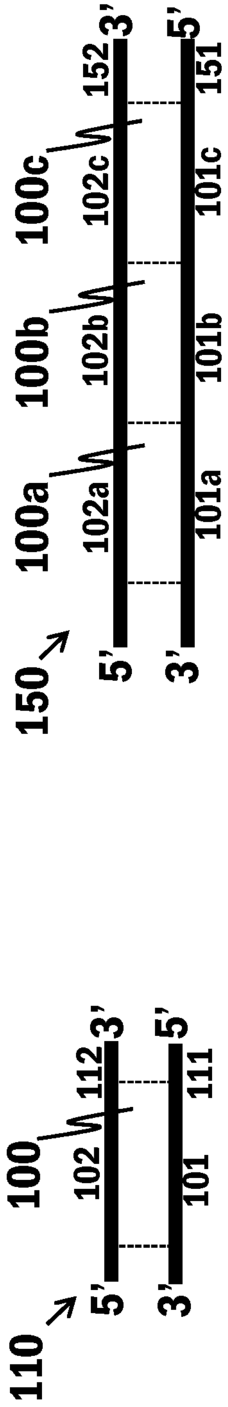
FIG. 1 is a general schematic of a method and processes provided herein. Panels 1A-1C show exemplary features and steps of methods provided herein.

It is noted that the drawings and elements therein are not necessarily drawn to shape or scale. For example, the shape or scale of elements of the drawings may be simplified or modified for ease or clarity of presentation. It should further be understood that the drawings and elements therein are for exemplary illustrative purposes only, and not be construed as limiting in any way.

DETAILED DESCRIPTION

While the invention includes various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention as defined by the claims.

In some embodiments, provided herein are methods and compositions relating to the amplification of nucleic acids and the generation of concatemers.

As used herein, a "polynucleotide" refers to a polymeric chain containing two or more nucleotides. "Polynucleotides" includes primers, oligonucleotides, nucleic acid strands, etc. A polynucleotide may contain standard or non-standard nucleotides. Typically, a polynucleotide contains a 5' phosphate at one terminus ("5' terminus") and a 3' hydroxyl group at the other terminus ("3' terminus) of the chain. The most 5' nucleotide of a polynucleotide may be referred to herein as the "5' terminal nucleotide" of the polynucleotide. The most 3' nucleotide of a polynucleotide may be referred to herein as the "3' terminal nucleotide" of the polynucleotide.

The term "downstream" as used herein in the context of a polynucleotide containing a 5' terminal nucleotide and a 3' terminal nucleotide refers to a position in the polynucleotide which is closer to the 3' terminal nucleotide than a reference position in the polynucleotide. For example, in a primer having the sequence: 5' ATAAGC 3', the "G" is downstream from the "T" and all of the "A"s.

The term "upstream" as used herein in the context of a polynucleotide containing a 5' terminal nucleotide and a 3' terminal nucleotide, refers to a position in the polynucleotide which is closer to the 5' terminal nucleotide than a reference position in the polynucleotide. For example, in a primer having the sequence: 5' ATAAGC 3', the "T" is upstream from the "G", the "C", and the two "A"s closest to the "G".

As used herein, "nucleic acid" includes both DNA and RNA, including DNA and RNA containing non-standard nucleotides. A "nucleic acid" contains at least one polynucleotide (a "nucleic acid strand"). A "nucleic acid" may be single-stranded or double-stranded.

As used herein, a "concatemer" refers to a nucleic acid molecule which contains within it two or more copies of a particular nucleic acid, wherein the copies are linked in series. Within the concatemer, the copies of the particular nucleic acid may be linked directly to each other, or they may be indirectly linked (e.g. there may be nucleotides between the copies of the particular nucleic acid). In an example, the particular nucleic acid may be that of a double-stranded nucleic acid template, such that a concatemer may contain two or more copies of the double-stranded nucleic acid template. In another example, the particular nucleic acid may be that of a polynucleotide template, such that a concatemer may contain two or more copies of the polynucleotide template. In some embodiments, concatemers generated according to methods and compositions provided herein may contain at least 2, 3, 4, 5, 6, 7, 8, 9, 10, 15, 20, 25, 50, 100 or more copies of a nucleic acid template directly linked to each other in series.

As used herein, a "target" nucleic acid or molecule refers to a nucleic acid of interest. A target nucleic acid/molecule may be of any type, including single-stranded or double stranded DNA or RNA (e.g. mRNA).

As used herein, "complementary" sequences refer to two nucleotide sequences which, when aligned anti-parallel to each other, contain multiple individual nucleotide bases which can pair with each other according to standard base-pairing rules (e.g. A-T, G-C, or A-U), such that molecules containing the sequences can specifically anneal to each other. It is not necessary for every nucleotide base in two sequences to be capable of pairing with each other for the sequences to be considered "complementary". Sequences may be considered complementary, for example, if at least 30%, 40%, 50%, 55%, 60%, 65%, 70%, 75%, 80%, 85%, 90%, 95%, 98%, 99%, or 100% of the nucleotide bases in two sequences can pair with each other when the sequences are optimally aligned for complementation. In addition, sequences may still be considered "complementary" when the total lengths of the two sequences are significantly different from each other. For example, a primer of 15 nucleotides may be considered "complementary" to a longer polynucleotide containing hundreds of nucleotides if multiple individual nucleotide bases of the primer can pair with nucleotide bases in the longer polynucleotide when the primer is aligned anti-parallel to a particular region of the longer polynucleotide. Additionally, "complementary" sequences may contain one or more nucleotide analogs or nucleobase analogs.

As used herein, the term "isolated" as applied to proteins, nucleic acids, or other biomolecules refers to a molecule that has been purified or separated from a component of its naturally-occurring environment (e.g. a protein purified from a cell in which it was naturally produced). An "isolated" molecule may be in contact with other molecules (for example, as part of a reaction mixture). As used herein, "isolated" molecules also include recombinantly-produced proteins or nucleic acids which have an amino acid or nucleotide sequence which occurs naturally. "Isolated" nucleic acids include polypeptide-encoding nucleic acid molecules contained in cells that ordinarily express the polypeptide where, for example, the nucleic acid molecule is at a chromosomal location different from that of natural cells. In some embodiments, "isolated" polypeptides are purified to at least 50%, 60%, 70%, 80%, 90%, 95%, 98%, or 100% homogeneity as evidenced by SDS-PAGE of the polypeptides followed by Coomassie blue, silver, or other protein staining method.

As used herein, a nucleic acid molecule which is described as containing the "sequence" of a template or other nucleic acid may also be considered to contain the template or other nucleic acid itself (e.g. a molecule which is described as containing the sequence of a template may also be described as containing the template), unless the context clearly dictates otherwise.

As used herein, when a first polynucleotide is described as "annealed", "annealing" or the like to a second polynucleotide, the entirety of the first polynucleotide or any portion thereof may anneal to the second polynucleotide, and vice versa.

As used herein, a reference to "treating" a given object to a condition or other object or the like refers to directly or indirectly exposing the given object to the recited condition or other object. Thus, while a "treating" step may involve a distinct related action (e.g. adding an enzyme to a vessel, shaking a vessel, etc.), not every "treating" step requires a distinct related action. For example, a reaction involving one or more reagents can be set up in a vessel, and once the reaction has been initiated, multiple events or steps may occur in the vessel without further human or mechanical intervention with the contents of the vessel. One or more of these multiple events or steps in the vessel may be described as "treating" an object in the vessel, even if no separate intervention with the contents of the vessel occurs after the initiation of the reaction.

Embodiments of methods and compositions provided herein may be described with reference to FIG. 1. A single template linear double-stranded nucleic acid 110 or multiple template linear double-stranded nuclei acid 150 may be provided (FIG. 1A). A single template linear double-stranded nucleic acid 110 contains a single copy of a double-stranded nucleic acid template 100. A multiple template linear double-stranded nucleic acid may contain two or more copies of a double-stranded nucleic acid template (e.g. 2, 3, 4, 5, 6, 7, 8, 9, 10, 15, 20, 25, 50, 100, or more). Exemplary multiple template linear double-stranded nucleic acid 150 contains 3 copies of the double-stranded nucleic acid template 100 (100*a*, 100*b*, and 100*c*). A double-stranded nucleic acid template comprises a first template strand 101 and a second template strand 102.

A single template linear double-stranded nucleic acid 110 contains a first strand 111 and a second strand 112. The sequence of the first template strand 101 is within the first strand 111 and the sequence of the second template strand 102 is within the second strand 112. A multiple template linear double-stranded nucleic acid 150 contains a first strand 151 and a second strand 152. The sequences of the multiple copies of the first template strand 101*a*, 101*b*, 101*c* are within the first strand 151 and the sequences of the multiple copies of the second template strand 102*a*, 102*b*, 102*c* are within the second strand 152.

Figure 1B:
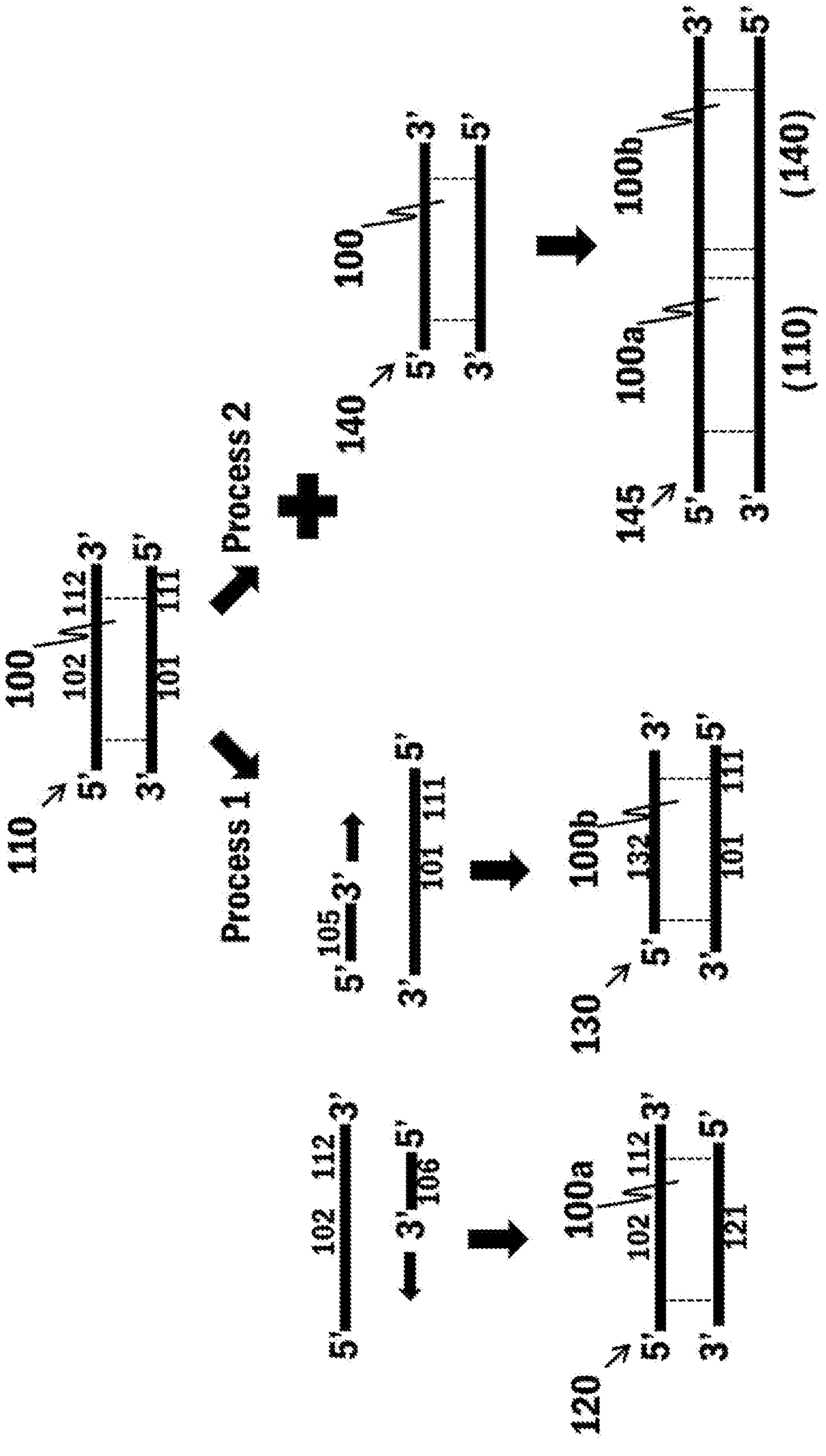
Figure 1C:
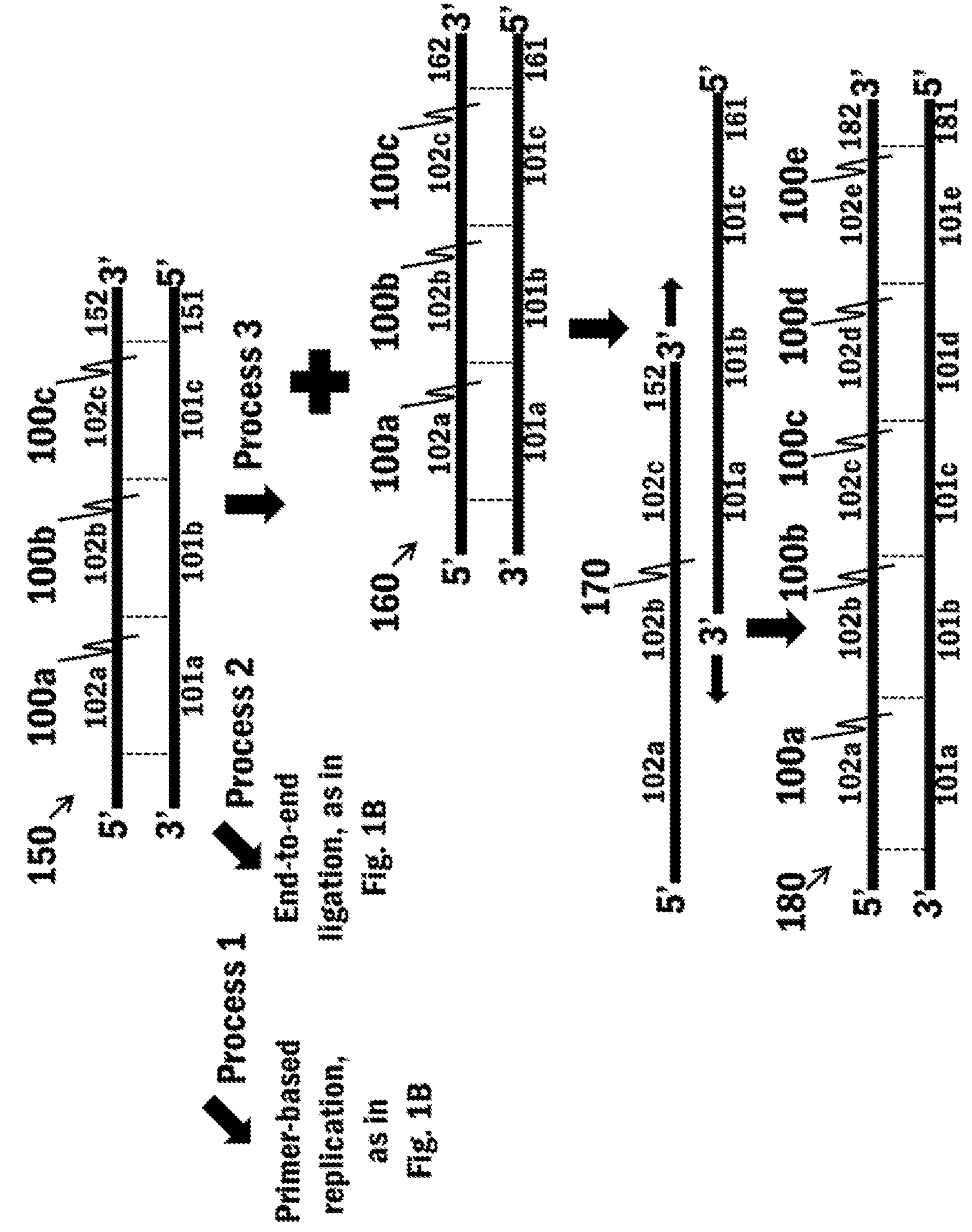

In some embodiments, a single template linear double-stranded nucleic acid 110 or multiple template linear double-stranded nuclei acid 150 may be treated under conditions such that at least 1 or 2 processes may occur with the single template linear double-stranded nucleic acid 110 (FIG. 1B) or at least 1, 2, or 3, processes may occur with the multiple template linear double-stranded nuclei acid 150 (FIG. 1C).

With reference to FIG. 1B, a single template linear double-stranded nucleic acid 110 may be treated such that it may undergo at least 1 or 2 different processes.

As a first alternative, the first 111 and second 112 strands are separated, the first template strand 101 and second template strand 102 are annealed with a first primer 105 or a second primer 106, respectively, and serve as a template for the nucleic acid polymerase-based generation of new template strands complementary to the respective template strand. Specifically, from the 3' terminus of the first primer 105, a new second template strand 132 may be synthesized which is complementary to the first template strand 101, and from the 3' terminus of the second primer 106, a new first template strand 121 may be synthesized which is complementary to the second template strand 102. This may result in the formation of two new single template linear double-stranded nucleic acids 120, 130, each of which contains a copy of the double-stranded nucleic acid template 100*a*, 100*b*. The first new single template linear double-stranded nucleic acid 120 contains the second template strand 102 and the new first template strand 121. The second new single template linear double-stranded nucleic acid 130 contains the first template strand 101 and the new second template strand 132. The above general process may be referred to herein as "primer-based replication".

In embodiments of primer-based replication, when the first 111 and second 112 strands are separated, initially, only a portion of the strands are separated, and the remaining portions of the strands remain annealed. In such embodiments, the first primer 105 or second primer 106 may anneal to a complementary exposed single-stranded portion of a strand, and then serve as the primer for the generation of a new second template strand 132 or a new first template strand 121, respectively. As the polymerase moves along the template strand (generating a new template strand), it may displace the strand which is annealed to the template strand (i.e. the polymerase may have strand displacement activity). The displaced template strand may then be annealed by a complementary primer thereof, from which a new template strand may be synthesized. Thus, in embodiments, the process of primer-based replication may be as generally outline as in "Process 1" of FIG. 1, except that the first template strand 101 and second template strand 102 are not simultaneously completely separated and each annealed with a primer, but instead, while portions of the first template strand and second template strand remain annealed to each other, a portion of one of the strands is annealed with a primer, and a polymerase then drives the separation of the two strands as a new template strand is synthesized.

As a second alternative, a single template linear double-stranded nucleic acid 110 may be treated under conditions such that it is ligated end-to-end with another double-stranded nucleic acid. Preferably, the other double-stranded nucleic acid is another copy of the single template linear double-stranded nucleic acid or a multiple template linear double-stranded nucleic acid (rather than a double-stranded nucleic acid which does not contain a copy of the template). The conditions may include incubating the double-stranded nucleic acids with a ligase. As an example, in FIG. 1B the single template linear double-stranded nucleic acid 110 is shown ligated end-to-end to another single template linear double-stranded nucleic acid 140, which results in the formation of a new multiple template linear double-stranded nucleic acid 145. The exemplary new multiple template linear double-stranded nucleic acid 145 contains two copies of the double-stranded nucleic acid template 100*a*, 100*b*—one from each of: i) single template linear double-stranded nucleic acid 110 and ii) single template linear double-stranded nucleic acid 140. The above general process may be referred to herein as "end-to-end ligation". New multiple template linear double-stranded nucleic acids formed by the end-to-end ligation process may contain any number of copies of the double-stranded nucleic acid template, based on the total number of copies of the double-stranded nucleic acid template in the molecules which are ligated together in an end-to-end ligation process. For example, if one multiple template linear double-stranded nucleic acid containing six copies of the template is ligated to one single template linear double-stranded nucleic acid, the new multiple template linear double-stranded nucleic acid will contain seven copies of the template.

Once a multiple template linear double-stranded nucleic acid is formed (e.g. as in the process of end-to-end ligation described in FIG. 1B), a multiple template linear double-stranded nucleic acid may participate in various processes. With reference to FIG. 1C, a multiple template linear double-stranded nucleic acid 150 may be treated such that it may undergo at least 1, 2, or 3 different processes. A multiple template linear double-stranded nucleic acid 150 as used in the processes of FIG. 1C may have been previously generated by any suitable mechanism, such as, for instance, it may be have been generated in an end-to-end ligation method as outlined in FIG. 1B, or it may have been generated in a previous round of concatemer generation as outlined in FIG. 1C and described further below. Also, while the exemplary multiple template linear double-stranded nucleic acid 150 of FIG. 1C contains 3 copies of the double-stranded nucleic acid template, a multiple template linear double-stranded nucleic acid may contain two or more copies of the double-stranded nucleic acid template, as described elsewhere herein.

As a first alternative, a multiple template linear double-stranded nucleic acid 150 may be treated to undergo primer-based replication as described above. The reaction conditions and reagents for primer-based replication with a multiple template linear double-stranded nucleic acid 150 may be the same as for with a single template linear double-stranded nucleic acid 110. With primer-based replication of a multiple template linear double-stranded nucleic acid, each new multiple template linear double-stranded nucleic acid formed as a result of the process may contain multiple copies of the double-stranded nucleic acid template. In the case of the multiple template linear double-stranded nucleic acid 150, each multiple template linear double-stranded nucleic acid contains 3 copies of the double-stranded nucleic acid template 100*a*, 100*b*, and 100*c*; accordingly, each new multiple template linear double-stranded nucleic acid generated from 150 may contain as many as 3 copies of the double-stranded nucleic acid template. However, since in some circumstances a primer may anneal to any copy of its complementary sequence in a multiple template linear double-stranded nucleic acid, new template strands which are complementary to a first or second strand of a multiple template linear double-stranded nucleic acid will not necessarily be as long as or contain as many copies of a template strand as the first or second strand of a multiple template linear double-stranded nucleic acid. For example, since multiple template linear double-stranded nucleic acid 150 contains 3 copies of the double-stranded nucleic acid template 100*a*, 100*b*, and 100*c*, if a primer anneals to a template strand of copy 100*b*, a new template strand generated from that primer will only contain 2 copies of the template strand.

As a second alternative, a multiple template linear double-stranded nucleic acid 150 may be treated to undergo end-to-end ligation with another double-stranded nucleic acid, as described above. Preferably, the other double-stranded nucleic acid is another copy of the single template linear double-stranded nucleic acid or a multiple template linear double-stranded nucleic acid (rather than a double-stranded nucleic acid which does not contain a copy of the template). A new multiple template linear double-stranded nucleic acid formed by the end-to-end ligation of a multiple template linear double-stranded nucleic acid plus another template linear double-stranded nucleic acid may contain as many copies of the double-stranded nucleic acid template as were collectively present in double-stranded nucleic acids which formed the new multiple template linear double-stranded nucleic acid. For example, if a first multiple template linear double-stranded nucleic acid which contains 3 copies of the double-stranded nucleic acid template is ligated end-to-end with a second multiple template linear double-stranded nucleic acid which contains 2 copies of the double-stranded nucleic acid template, the resulting new multiple template linear double-stranded nucleic acid will contain 5 copies of the double-stranded nucleic acid, template. In another example, if a multiple template linear double-stranded nucleic acid which contains 2 copies of the double-stranded nucleic acid template is ligated end-to-end with a single template linear double-stranded nucleic acid, the resulting new multiple template linear double-stranded nucleic acid will contain 3 copies of the double-stranded nucleic acid template.

As a third alternative, a multiple template linear double-stranded nucleic acid 150 may be treated with another multiple template linear double-stranded nucleic acid 160 under conditions such that a cross-over structure 170 comprising a 3' terminal region of a strand of the multiple template linear double-stranded nucleic acid 150 annealed to a 3' terminal region of a strand of the multiple template linear double-stranded nucleic acid 160 is formed. Specifically, the multiple template linear double-stranded nucleic acid 150 contains a first strand 151 and a second strand 152, and three copies of the double-stranded nucleic acid template 100*a*, 100*b*, 100*c*, and the multiple template linear double-stranded nucleic acid 160 contains a first strand 161 and a second strand 162, and three copies of the double-stranded nucleic acid template 100*a*, 100*b*, 100*c*. Each copy of the double-stranded nucleic acid template (whether in multiple template linear double-stranded nucleic acids 150 or in 160) contains a copy of the first template strand 101 and a copy of the second template strand 102. The multiple template linear double-stranded nucleic acids 150, 160 may be treated under conditions such that, for example, the sequence of the first template strand 101*a* of the first strand of multiple template linear double-stranded nucleic acid 161 anneals to the sequence of second template strand 102*c* of the second strand of multiple template linear double-stranded nucleic acid 152, to produce a cross-over structure comprising these strands. In general, since multiple template linear double-stranded nucleic acids each contain at least two copies of the double-stranded nucleic acid template, there are a plurality of regions within any given multiple template linear double-stranded nucleic acids which may be complementary to another multiple template linear double-stranded nucleic acids, thus facilitating the formation of cross-over structures between different multiple template linear double-stranded nucleic acids. A cross-over structure 170 may be treated with a nucleic acid polymerase under conditions such an extension product of the first strand of multiple template linear double-stranded nucleic acid 161 and an extension product of the second strand of multiple template linear double-stranded nucleic acid 152 are formed. The polymerase may generate an extension product from the 3' terminus of the nucleic acid strands 161, 152. The extension product of the first strand of multiple template linear double-stranded nucleic acid 161 may be referred to herein as a "new concatemer first strand" 181. The extension product of the second strand of multiple template linear double-stranded nucleic acid 152 may be referred to herein as a "new concatemer second strand" 182. Together, the new concatemer first strand 181 and new concatemer second strand 182 may be referred to as a "new concatemer" 180. The new concatemer 180 may have a greater nucleotide length than either of the parent molecules used to generated the new concatemer 180, and may contain more copies of the double-stranded nucleic acid template. For example, new concatemer 180 contains 5 copies of the double-stranded nucleic acid template 100*a*, 100*b*, 100*c*, 100*d*, and 100*e*. A new concatemer may exclusively contain copies of the double-stranded nucleic acid template, or it may contain nucleotides in addition to copies of the double-stranded nucleic acid template. The above general process may be referred to herein as "cross-over strand replication".

In some embodiments, in methods provided herein, one or more of the above processes may simultaneously occur in the same reaction mixture. In some embodiments, all of the above processes may simultaneously occur in the same reaction mixture. In addition, a molecule generated according to a process provided herein may then be used in the same or another process provided herein. For example, if a multiple template linear double-stranded nucleic acid is generated from two single template linear double-stranded nucleic acids, that multiple template linear double-stranded nucleic acid may undergo any of the processes described herein for multiple template linear double-stranded nucleic acid. In another example, a molecule formed by an end-to-end ligation process provided herein may then be used as a template for a primer-based replication process. In another example, a new concatemer formed by a cross-over strand based replication process may then be used as part of an end-to-end ligation process. In another example, 2, 3, 4, 5, or more double-stranded nucleic acids maybe simultaneously ligated into a single molecule in an end-to-end ligation process provided herein.

In some embodiments, methods provided herein may lead to an increase in a reaction mixture of one or both of: 1) the number of nucleic acid molecules containing a double-stranded nucleic acid template of interest, and 2) the average number of copies of the double-stranded nucleic acid template of interest present in nucleic acid molecules containing double-stranded nucleic acid template of interest. Accordingly, in some embodiments, double-stranded nucleic acid templates may be rapidly amplified according to methods and processes provided herein. For example, in some embodiments, a nucleic acid template may be amplified (i.e. increased in number) at least 500-fold within 0.1, 0.5, 1, 3, 5, 10, 15, 20, 30, 40, 50, 60, 90, 120, or 180 minutes of starting the method. In another example, in some embodiments, a nucleic acid template may be amplified at least 10,000-fold within 0.1, 0.5, 1, 3, 5, 10, 15, 20, 30, 40, 50, 60, 90, 120, or 180 minutes of starting the method. In another example, in some embodiments, a nucleic acid template may be amplified at least 5, 10, 25, 50, 100, 250, 500, 1,000, 5,000, 10,000, 50,000, 100,000, 500,000, or 1,000,000-fold over the original amount of the nucleic acid template present in a reaction mixture at the start of the method within 0.1 minute, 0.5 minute, 1 minute, 3 minutes, 5 minutes, 10 minutes, 15 minutes, 20 minutes, 30 minutes, 40 minutes, 50 minutes, 60 minutes, 90 minutes, 2 hours, 3 hours, 4 hours, 6 hours, 8 hours, 12 hours, 16 hours, or 24 hours of initiation of the method. In some embodiments, when a method is initiated, all of the reagents for a process of the method are in a vessel containing the reaction mixture for the method. In some embodiments, when a method is initiated, all of the reagents for all of the processes of the method are in a vessel containing the reaction mixture for the method.

In some embodiments, in a method provided herein, a nucleic acid template may be amplified at greater than a linear rate. In some embodiments, in a method provided herein, a nucleic acid template may be amplified exponentially. In some embodiments, in a method provided herein, a nucleic acid template may at least double in number every 1, 2, 3, 5, 10, 15, 20, 25, 30, 45, 60, 90, 120, 180, or 240 minutes after the initiation of the method. In some embodiments, a nucleic acid template may amplified at least 5, 10, 25, 50, 100, 250, 500, 1,000, 5,000, 10,000, 50,000, 100,000, 500,000, 1,000,000, or 10,000,000-fold over the original amount of the nucleic acid template present in the reaction at the start of the method.

The presence of multiple copies of a nucleic acid template in a concatemer or other multiple template linear double-stranded nucleic acid generated according to a method provided herein may contribute to the rapid amplification of nucleic acid templates according to methods provided herein. In particular, since multiple copies of a strand of a nucleic acid template may be present in a single concatemer/multiple template linear double-stranded nucleic acid strand, the loading of a single polymerase onto a single concatamer/multiple template linear double-stranded nucleic acid strand may result in the generation of multiple copies of a strand of the nucleic acid template. In some situations, the time required for nucleic acid polymerases to encounter and load onto nucleic acid strands may significantly impact the overall speed of an amplification reaction. For example, if each nucleic acid strand that a polymerase encounters during a replication reaction only contains a single copy of a strand of a nucleic acid template, a polymerase may need to encounter and load onto a new template strand after each copy of the strand of the template is generated. In contrast, with a concatemer, after the polymerase encounters and loads on a concatemer strand, it may synthesize multiple copies of a strand of the template without needing to leave the concatemer strand or encounter and load onto another strand.

In methods provided herein, double-stranded nucleic acids which do not contain a double-stranded template of interest may sometimes be joined as part of an end-to-end ligation process provided herein. However, since these molecules will generally not be specifically amplified by a polymerase with the processes provided herein (due to the lack of primers which specifically anneal to the double-stranded template of interest), these molecules will not be specifically amplified with methods provided herein. Also, since these molecules are not specifically amplified with methods provided herein, as methods provided herein progress, increasing numbers of double-stranded nucleic acids which contain the double-stranded template of interest may be present in a reaction mixture (e.g. due to their generation by primer-based processes). Thus, as reactions provided herein progress, an increasing percentage of double-stranded molecules in a reaction may contain the double-stranded template of interest, thus further increasing the likelihood that an end-to-end ligation event will be between two double-stranded nucleic acids which each contain at least one copy of the double-stranded template of interest (rather than between two double-stranded nucleic acid which don't contain the template of interest or between one double-stranded nucleic acid which contains the template and one double-stranded nucleic acid which doesn't contain the template of interest). Accordingly, the methods provided herein permit the rapid and specific amplification of double-stranded templates of interest.

In some embodiments of methods provided herein, the various processes described herein involving a double-stranded nucleic acid template are equally likely to occur. In other embodiments, one or more the processes are more or less likely to occur. In some embodiments, under certain reaction conditions the various processes described herein involving a double-stranded nucleic acid template are equally likely to occur. In some embodiments, under certain reaction conditions one or more of the processes are more or less likely to occur. For example, in a method provided herein involving a nucleic acid polymerase and a ligase, the polymerase and the ligase may have different optimal temperatures for activity. If the reaction is incubated at a temperature closer to the optimal temperature for the polymerase, then polymerase-based processes described herein (primer-based replication and cross-over strand-based replication) may be favored over end-to-end ligation. In some examples, methods provided herein may be performed at two or more temperatures, in order to promote the occurrence of different processes provided herein in a reaction mixture (e.g. based on different optimal temperatures for different enzymes).

In processes described herein involving a nucleic acid polymerase, the polymerase may have strand displacement activity. For example, in primer-based replication processes described herein, as a polymerase generates an extension product from the primer along one strand of the double-stranded nucleic acid template, it may displace the other strand of the double-stranded nucleic acid template from the one strand, as the two strands may still be partially annealed at the start of the generation of the extension product of the primer. In another example, in a cross-over strand replication process described herein, as a polymerase generates an extension product from the 3' end of a strand of a multiple template linear double-stranded nucleic acid in a cross-over structure, the polymerase may displace the other original strand of the multiple template linear double-stranded nucleic acid. During the generation of an extension product of a polymerase, the extension product may become covalently linked to the original molecule which served as the primer for the generation of the extension product (e.g. a primer or larger nucleic acid strand). In some situations, the molecule which served as the primer for the generation of an extension product of a polymerase may be considered to be part of the extension product of the polymerase. In some embodiments, conditions such that an extension product of a primer or other nucleic acid strand may be formed may include any condition sufficient to support polymerase-based nucleic acid synthesis. Example conditions for polymerase-based nucleic acid synthesis are known in the art and are provided, for example, in Molecular Cloning: A Laboratory Manual, M. R. Green and J. Sambrook, Cold Spring Harbor Laboratory Press (2012), which is herein incorporated by reference in its entirety. The same or different types of polymerases may be used for the different processes in methods provided herein.

Nucleic acid molecules generated according to methods and compositions provided herein may be of any length of nucleotides. In some embodiments, nucleic acid molecules generated herein may be at least 30, 40, 50, 60, 70, 80, 90, 100, 150, 200, 250, 300, 400, 500, 600, 700, 800, 900, 1000, 1500, 2000, 3000, 4000, 5000, 6000, 7000, 8000, 9000, 10,000, 15,000, 20,000, or 25,000 nucleotides in length. In some embodiments, nucleic acid molecules generated herein may be no more than 30, 40, 50, 60, 70, 80, 90, 100, 150, 200, 250, 300, 400, 500, 600, 700, 800, 900, 1000, 1500, 2000, 3000, 4000, 5000, 6000, 7000, 8000, 9000, 10,000, 15,000, 20,000, or 25;000 nucleotides in length. In some embodiments, nucleic acid molecules generated herein may have a length selected from a range having a minimum value of 30, 40, 50, 60, 70, 80, 90, 100, 150, 200, 250, 300, 400, 500, 600, 700, 800, 900, 1000, 1500, 2000, 3000, 4000, 5000, 6000, 7000, 8000, 9000, 10,000, 15,000, or 20,000 nucleotides in length, and a maximum value of 40, 50, 60, 70, 80, 90, 100, 150, 200, 250, 300, 400, 500, 600, 700, 800, 900, 1000, 1500, 2000, 3000, 4000, 5000, 6000, 7000, 8000, 9000, 10,000, 15,000, 20,000, or 25,000 nucleotides in length. In some embodiments, at least some nucleic acid molecules generated according to a method or composition provided herein have characteristics described above. In some embodiments, at least 10%, 20%, 30%, 40%, 50%, 60%, 70%, 80%, 90%, or 95% of nucleic acid molecules generated according to a method or composition provided herein have characteristics described above.

Nucleic acid molecules generated according to methods and compositions provided herein may contain any number of copies of a double-stranded nucleic acid template. In some embodiments, nucleic acid molecules generated herein may contain at least 2, 3, 4, 5, 6, 7, 8, 9, 10, 11, 12, 13, 14, 15, 16, 17, 18, 19, 20, 25, 30, 35, 40, 45, 50, 60, 70, 80, 90, or 100 copies of a double-stranded nucleic acid template. In some embodiments, nucleic acid molecules generated herein may contain no more than 2, 3, 4, 5, 6, 7, 8, 9, 10, 11, 12, 13, 14, 15, 16, 17, 18, 19, 20, 25, 30, 35, 40, 45, 50, 60, 70, 80, 90, or 100 copies of a double-stranded nucleic acid template. In some embodiments, nucleic acid molecules generated herein may have a number of copies of a double-stranded nucleic acid template selected from a range having a minimum value of 2, 3, 4, 5, 6, 7, 8, 9, 10, 11, 12, 13, 14, 15, 16, 17, 18, 19, 20, 25, 30, 35, 40, 45, 50, 60, 70, 80, or 90 copies, and a maximum value of 3, 4, 5, 6, 7, 8, 9, 10, 11, 12, 13, 14, 15, 16, 17, 18, 19, 20, 25, 30, 35, 40, 45, 50, 60, 70, 80, 90, or 100 copies. In some embodiments, at least some nucleic acid generated according to a method or composition provided herein have characteristics described above. In some embodiments, at least 10%, 20%, 30%, 40%, 50%, 60%, 70%, 80%, 90%, or 95% of nucleic acid generated according to a method or composition provided herein have characteristics described above.

Progress of a method provided herein may be monitored in multiple different ways. In embodiments, a reaction may be assayed for a nucleic acid amplification product (e.g. for the amount of the product or the rate of its generation). In other embodiments, a reaction may be assayed for the activity of a polymerase along a nucleic acid template (e.g. for movement of a polymerase along a template strand). Thus, in some embodiments, events of a method provided herein may observed due to the accumulation of product from a method (which may be during or after completion of steps of the method), or due to detectable events occurring during the steps of a method.

The presence of amplified nucleic acids can be assayed, for example, by detection of reaction products (amplified nucleic acids or reaction by-products) or by detection of probes associated with the reaction progress.

In some embodiments, reaction products may be identified by staining the products with a dye. In some embodiments, a dye may have greater fluorescence when bound to a nucleic acid than when not bound to a nucleic acid. In some embodiments, a dye may intercalate with a double-stranded nucleic acid or it may bind to an external region of a nucleic acid. Nucleic acid dyes that may be used with methods and compositions provided herein include, for example, cyanine dyes, PicoGreen®, OliGreen®, RiboGreen®, SYBR® dyes, SYBR® Gold, SYBR® Green I, SYBR® Green II, ethidium bromide, dihydroethidium, BlueView™, TOTO® dyes, TO-PRO® dyes, POPO® dyes, YOYO® dyes, BOBO® dyes, JOJO® dyes, LOLO® dyes, SYTOX® dyes, SYTO® dyes, propidium iodide, hexidium iodide, methylene blue, DAPI, acridine orange, quinacrine, acridine dimers, 9-amino-6-chloro-2-methoxyacridine, bisbenzimide dyes, Hoechst dyes, 7-aminoactinomycin D, actinomycin D, hydroxystilbamidine, pyronin Y, Diamond™ dye, GelRed™, GelGreen™ and LDS 751.

In some embodiments, reaction products may be identified by analysis of turbidity of amplification reactions. For example, in embodiments, increased turbidity may be correlated with formation of reaction products and reaction by-products (e.g. pyrophosphate complexed with magnesium).

In some embodiments, reaction products may be identified by separating a reaction performed according to a method herein by gel electrophoresis, followed by staining of the gel with a dye for nucleic acids. The dye may be any nucleic acid dye disclosed herein or otherwise known in the art.

In some embodiments, any method or composition known in the art for the detection of nucleic acids or processes associated with the generation of nucleic acids may be used with methods and compositions provided herein.

In some embodiments, a nucleic acid probe which contains a nucleotide sequence complementary to a portion of a nucleic acid template strand (or strand having a similar or identical sequence) and which contains one or both of a fluorescent reporter (fluorophore) and a quencher are included in a reaction provided herein.

In an example, a nucleic acid probe may contain a fluorescent reporter at its 5' or 3' terminus, and a quencher at the other terminus. The probe may further have a nucleotide sequence containing, in order, at least a first, second, and third region, where the first and third regions are complementary to each other, and where at least a portion of the second region is complementary to a portion of a strand of the nucleic acid template (the probe "detection sequence"). In some embodiments, the length of the second region may be greater than the length of the first or third regions. In some embodiments, the length of the second region may be between 10 and 40 nucleotides, and the length of first and third regions may be between 4 and 10 nucleotides. The probe may have at least two different conformations: (A) a conformation where the probe is not annealed to its detection sequence and where the first and third regions are annealed to each other; this conformation may be a "stem-loop" structure, where the first and third regions form the stem and the second region forms the loop, and (B) a conformation where the probe is annealed to its detection sequence; in this conformation, the second region or a portion thereof is annealed to its detection sequence and the first and third regions are not annealed to each other. In conformation (A) of the probe, the fluorescent reporter and quencher (which are located at opposite termini of the probe/at the outer ends of the first and third regions) may be in close proximity to each other (both being at the end of the stem structure formed by the annealing of the first and third regions), such that the fluorescent reporter is quenched. In conformation (B) of the probe, the fluorescent reporter and quencher may not be in close proximity to each other, such that the fluorescent reporter is not quenched. The probe may be used to monitor accumulation of a selected reaction product, for example, under reaction conditions where the probe may either form a stem-loop structure or anneal to its detection sequence. In some embodiments, if the detection sequence is present, the probe may anneal to the detection sequence, and the probe may fluoresce in response to light of a wavelength of the fluorophore's excitation spectrum. In contrast, if the detection sequence is not present, the probe may form a stem-loop structure, and not fluoresce in response to light of a wavelength of the fluorophore's excitation spectrum.

In another example, a nucleic acid probe may contain a fluorescent reporter at its 5' or 3' terminus, and it may be annealed to a nucleic acid primer containing a quencher. The nucleic acid primer containing a quencher may contain the quencher at a position in the primer such that when the nucleic acid probe is annealed to the primer, the fluorescent reporter is quenched. The probe may be used to monitor accumulation of a selected reaction product, for example, under reaction conditions where the probe may either anneal to the primer or anneal to its detection sequence. In some embodiments, if the detection sequence is present, the probe may anneal to the detection sequence, and the probe may fluoresce in response to light of a wavelength of the fluorophore's excitation spectrum. In contrast, if the detection sequence is not present, theprobe may remain paired with the primer, and not fluoresce in response to light of a wavelength of the fluorophore's excitation spectrum.

In probes containing a fluorescent reporter and quencher pair, the fluorescent reporter and quencher may be selected so that the quencher can effectively quench the reporter. In some embodiments, a fluorescent reporter is paired with a quencher where the emission maximum of the fluorescent reporter is similar to the absorption maximum of the quencher. Fluorophores that may be used as the fluorescent reporter include, for example, CAL Fluor Gold, CAL Fluor Orange, Quasar 570, CAL Fluor Red 590, CAL Fluor Red 610, CAL Fluor Red 610, CAL Fluor Red 635, Quasar 670 (Biosearch Technologies), VIC, NED (Life Technologies), Cy3, Cy5, Cy5.5 (GE Healthcare Life Sciences), Oyster 556, Oyster 645 (Integrated DNA Technologies), LC red 610, LC red 610, LC red 640, LC red 670, LC red 705 (Roche Applies Science), Texas red, FAM, TET, HEX, JOE, TMR, and ROX. Quenchers that may be used include, for example, DDQ-I, DDQ-II (Eurogentec), Eclipse (Epoch Biosciences), Iowa Black FQ, Iowa Black RQ (Integrated DNA Technologies), BHQ-1, BHQ-2, BHQ-3 (Biosearch Technologies), QSY-7, QSY-21 (Molecular Probes), and Dabcyl.

In some embodiments, a method provided herein may be monitored in an apparatus containing a light source and an optical sensor. In some situations, the reaction may be positioned in the path of light from the light source, and light absorbed by the sample (e.g. in the case of a turbid reaction), scattered by the sample (e.g. in the case of a turbid reaction), or emitted by the sample (e.g. in the case of a reaction containing a fluorescent molecule) may be measured. In some embodiments, a method provided herein may be performed or monitored in a device or module therein as disclosed in U.S. patent application Ser. No. 13/769,779, filed Feb. 18, 2013, which is herein incorporated by reference in its entirety.

Using methods provided herein, specific amplification products of a nucleic acid template of interest may be identified within, for example, 30 seconds, 1 minute, 3 minutes, 5 minutes, 10 minutes, 15 minutes, 20 minutes, 30 minutes, 45 minutes, 60 minutes, 90 minutes, 120 minutes, 180 minutes, or 240 minutes of initiation of an amplification reaction. In other examples, using methods provided herein, amplification reactions which are positive for a nucleic acid template of interest may be identified when as few as 10, 50, 100, 500, 1000, 5000, 10,000, 50,000, 100,000, 500,000, or 1,000,000 copies of the template are generated. In other examples, using methods provided herein, the presence of a nucleic acid template of interest in a sample containing as few as 1, 2, 3, 4, 5, 10, 15, 20, 25, 30, 40, 50, 100, 200, 500, 1000, 5000, or 10,000 copies of the template of interest at the start of the method may be identified.

In embodiments, methods provided herein may be used to assay a sample for a target nucleic acid of interest. In certain embodiments, the presence or quantity of a target nucleic acid of interest in a sample may be determined by a method involving determining an inflection time for nucleic acid amplification in a reaction. An inflection time/inflection point is a time or a point where an amplification reaction is determined as being positive for a nucleic acid template. An inflection time/point may be identified by one or more indicators, such as for example, the time post-initiation of a reaction when a selected quantity of nucleic acid has been generated in the reaction, the time when the rate of amplification in a reaction changes from a baseline phase to an exponential phase, or the time when the rate of amplification in a reaction changes from an exponential phase to a plateau phase, etc. In embodiments, an inflection time/point may be identified based on a change in fluorescence or absorbance of a reaction, or upon the fluorescence or absorbance of a reaction reaching a selected value. In certain embodiments, the presence or quantity of a target nucleic acid of interest in a sample may be determined by a method involving comparison of an inflection time for nucleic acid amplification of a reaction of which has an unknown amount of target nucleic acid of interest versus one or both of: i) a reaction which is known to lack the target nucleic acid of interest (i.e. a negative control) or ii) a reaction which is known to contain the target nucleic acid of interest (i.e. a positive control). In embodiments, both a reaction which contains the target nucleic acid of interest and a reaction which does not contain the target nucleic acid may be measured for a selected inflection time. In embodiments, the presence of a target nucleic acid of interest in a sample may be determined based on a method which involves evaluation of the difference in time between inflection of a reaction containing a sample which may or may not contain a target nucleic acid of interest, and a time of inflection of one or more reactions with known target nucleic acid of interest status (e.g. which are known to contain or not contain the target nucleic acid of interest). For example, a sample may be identified as containing a target nucleic acid of interest if the inflection time of the reaction according to a method provided herein is at least 3, 5, 10, 15, 20, 30, 40, 50, 60, 90, 120, or 180 minutes earlier than a corresponding reaction which is known to not contain the target nucleic acid of interest. In another example, a sample may be identified as containing a target nucleic acid of interest if the inflection time of the reaction according to a method provided herein is no more than 3, 5, 10, 15, 20, 30, 40, 50, 60, 90, 120, or 180 minutes later than a corresponding reaction which is known to contain the target nucleic acid of interest.

Methods provided herein may be performed for any length of time. Typically, the method will be performed for a length of time sufficient to monitor, for example, the rate of nucleic acid replication, the occurrence of polymerase activity, or the accumulation of amplification product. In some embodiments, a method provided herein may be performed for a total of less than 10 seconds, 30 seconds, 1 minute, 5 minutes, 10 minutes, 20 minutes, 30 minutes, 45 minutes, 1 hour, 2 hours, 3 hours, 4 hours, 6 hours, 8 hours, 12 hours, 16 hours, or 24 hours, by which time the rate of nucleic acid replication, the occurrence of polymerase activity, or the accumulation of amplification product is measured.

Methods provided herein may be terminated in various ways. In one embodiment, steps of a method may end upon the reduction in concentration or complete consumption of one or more reagents involved in one or more steps of the method (e.g. dNTPs). In another embodiment, steps of a method may end upon inactivation of one or more enzymes involved in one or more steps of the method (e.g. polymerases). Enzymes may be inactivated by various ways. For example, enzymes may gradually lose enzymatic activity over time due to random events that affect the structure of the enzyme, or enzymes may be exposed to a condition to accelerate the inactivation of the enzyme activity (e.g. high heat, extreme pH, etc.).

A single template linear double-stranded nucleic acid comprises a single copy of a double-stranded nucleic acid template. In some embodiments, the entirety of the single template linear double-stranded nucleic acid is a double-stranded nucleic acid template. In some embodiments, a single template linear double-stranded nucleic acid contains nucleotides in addition to the double-stranded nucleic acid template. In some embodiments, a multiple template linear double-stranded nucleic acid comprises only copies of the double-stranded nucleic acid template. In some embodiments, a multiple template linear double-stranded nucleic acid contains nucleotides in addition to the double-stranded nucleic acid templates. Typically, template linear double-stranded nucleic acids provided herein have blunt ends. In some embodiments, template linear double-stranded nucleic acids may have sticky ends. ("sticky ends" refer to ends having an overhanging strand having one or more unpaired nucleotides). A template linear double-stranded nucleic acid may contain DNA, RNA, or a mixture thereof.

A single template linear double-stranded nucleic acid may be generated by any process wherein a double-stranded nucleic acid containing a single copy of a double-stranded nucleic template may be formed. For example, a single template linear double-stranded nucleic acid may be generated from a previous single template linear double-stranded nucleic acid according to a primer-based replication process described herein. In another example, a single template linear double-stranded nucleic acid may be generated from a circular nucleic acid containing the sequence of the double-stranded nucleic template, by a primer-based replication process. In another example, a single template linear double-stranded nucleic acid may be generated from a single-stranded RNA molecule, through a process involving a reverse transcriptase. In another example, a single template linear double-stranded nucleic acid may be generated by the end-to-end ligation of double-stranded nucleic acid that does not contain a copy of the double-stranded nucleic acid template with a previous single template linear double-stranded nucleic acid. A multiple template linear double-stranded nucleic acid may be generated by any process wherein a double-stranded nucleic acid containing a two or more copies of a double-stranded nucleic template may be formed, such as by the processes described herein. As used herein, the term "template linear double-stranded nucleic acid" includes both single template linear double-stranded nucleic acids and multiple template linear double-stranded nucleic acids.

A template linear double-stranded nucleic acid may be of any length of nucleotides. For example, a template linear double-stranded nucleic acid may be at least 2, 3, 4, 5, 6, 7, 8, 9, 10, 12, 14, 16, 18, 20, 25, 30, 35, 40, 45, 50, 60, 70, 80, 90, 100, 150, 200, 250, 300, 350, 400, 500, 750, 1000, or 1500 nucleotides in length. In another example, a template linear double-stranded nucleic acid may be between 2 and 100,000, between 5 and 100,000, between 10 and 100,000, between 15 and 100,000, between 20 and 100,000, between 25 and 100,000, between 30 and 100,000, between 50 and 100,000, between 70 and 100,000, between 100 and 100,000, between 200 and 100,000, between 2 and 10,000, between 5 and 10,000, between 10 and 10,000, between 15 and 10,000, between 20 and 10,000, between 25 and 10,000, between 30 and 10,000, between 50 and 10,000, between 70 and 10,000, between 100 and 10,000, between 200 and 10,000, between 2 and 5,000, between 5 and 5,000, between 10 and 5,000, between 15 and 5,000, between 20 and 5,000, between 25 and 5,000, between 30 and 5,000, between 50 and 5,000, between 70 and 5,000, between 100 and 5,000, between 200 and 5,000, between 2 and 3,000, between 5 and 3,000, between 10 and 3,000, between 15 and 3,000, between 20 and 3,000, between 25 and 3,000, between 30 and 3,000, between 50 and 3,000, between 70 and 3,000, between 100 and 3,000, between 200 and 3,000, between 2 and 1,000, between 5 and 1,000, between 10 and 1,000, between 15 and 1,000, between 20 and 1,000, between 25 and 1,000, between 30 and 1,000, between 50 and 1,000, between 70 and 1,000, between 100 and 1,000, between 200 and 1,000, between 2 and 500, between 5 and 500, between 10 and 500, between 15 and 500, between 20 and 500, between 25 and 500, between 30 and 500, between 50 and 500, between 70 and 500, between 100 and 500, or between 200 and 500 nucleotide bases in length.

A double-stranded nucleic acid template may be generated by any method provided herein for the generation of a template linear double-stranded nucleic acid provided herein.

In some embodiments, a double-stranded nucleic acid template is a double-stranded DNA molecule that was generated from an RNA molecule (e.g. a single stranded RNA molecule, such as mRNA). A double-stranded DNA molecule may be generated from an RNA molecule through techniques that are well-known in the art, for example, through reverse transcription. Example conditions for generating a double-stranded DNA molecule from an RNA molecule are provided, for example, in RNA: A Laboratory Manual, D. Rio et al., Cold Spring Harbor Laboratory Press (2011), which is herein incorporated by reference in its entirety. Briefly, in some examples, a primer which is complementary to an RNA sequence of interest may be incubated with: reverse transcriptase enzyme (e.g. AMV reverse transcriptase, M-MLV reverse transcriptase, Superscript II™ reverse transcriptase, Superscript III™ reverse transcriptase, or ThermoScript™ reverse transcriptase), dNTPs, and the RNA sequence of interest. The primer may anneal to the RNA, and then, starting from the 3' end of the primer, the reverse transcriptase may synthesize a strand of DNA complementary to the RNA (cDNA). In some embodiments, the RNA annealed to the cDNA may be degraded (e.g. with an RNase; the RNase may be the reverse transcriptase, which may also have RNase activity), and the cDNA may then be incubated with: a different primer which is complementary to the strand of cDNA, dNTPs, and a DNA polymerase (e.g. any DNA polymerase discussed elsewhere herein). Then, starting from the 3' end of the different primer, the DNA polymerase may synthesize a strand of DNA complementary to cDNA, thereby generating a linear double-stranded DNA molecule.

In some embodiments, a double-stranded nucleic acid template may be generated from a single-stranded RNA molecule in the same reaction mixture in which the double-stranded nucleic acid template is amplified according to a method provided herein. In some embodiments, the same primer may be used for both A) generation of a cDNA strand from an RNA molecule, and B) as a first or second primer in primer-based replication process provided herein.

In some embodiments, a nucleic acid template may be single stranded or double-stranded. A single strand of a nucleic acid template may be referred to herein as a "polynucleotide template". A "polynucleotide template" as referred to herein is not precluded from binding to a complementary sequence thereof. In other words, a "polynucleotide template" may be, for example, the entirety of a single-stranded nucleic acid template, or it may be one strand of a double-stranded nucleic acid template.

A double-stranded nucleic acid template may be of any length of nucleotides. For example, a double-stranded nucleic acid template may be at least 2, 3, 4, 5, 6, 7, 8, 9, 10, 12, 14, 16, 18, 20, 25, 30, 35, 40, 45, 50, 60, 70, 80, 90, 100, 150, 200, 250, 300, 350, 400, 500, 750, 1000, or 1500 nucleotides in length. In another example, a double-stranded nucleic acid template may be between 2 and 100,000, between 5 and 100,000, between 10 and 100,000, between 15 and 100,000, between 20 and 100,000, between 25 and 100,000, between 30 and 100,000, between 50 and 100,000, between 70 and 100,000, between 100 and 100,000, between 200 and 100,000, between 2 and 10,000, between 5 and 10,000, between 10 and 10,000, between 15 and 10,000, between 20 and 10,000, between 25 and 10,000, between 30 and 10,000, between 50 and 10,000, between 70 and 10,000, between 100 and 10,000, between 200 and 10,000, between 2 and 5,000, between 5 and 5,000, between 10 and 5,000, between 15 and 5,000, between 20 and 5,000, between 25 and 5,000, between 30 and 5,000, between 50 and 5,000, between 70 and 5,000, between 100 and 5,000, between 200 and 5,000, between 2 and 3,000, between 5 and 3,000, between 10 and 3,000, between 15 and 3,000, between 20 and 3,000, between 25 and 3,000, between 30 and 3,000, between 50 and 3,000, between 70 and 3,000, between 100 and 3,000, between 200 and 3,000, between 2 and 1,000, between 5 and 1,000, between 10 and 1,000, between 15 and 1,000, between 20 and 1,000, between 25 and 1,000, between 30 and 1,000, between 50 and 1,000, between 70 and 1,000, between 100 and 1,000, between 200 and 1,000, between 2 and 500, between 5 and 500, between 10 and 500, between 15 and 500, between 20 and 500, between 25 and 500, between 30 and 500, between 50 and 500, between 70 and 500, between 100 and 500, or between 200 and 500 nucleotide bases in length.

A "primer" as used herein may refer to a polynucleotide which is i) capable of hybridizing to an original nucleic acid strand and ii) acting as a point of initiation for the synthesis of a new nucleic acid strand, wherein the new nucleic acid strand is an extension product of the primer and is complementary to the original strand. A primer may have a free —OH group at its 3' terminus, which may serve as the origin of synthesis for the extension product.

A primer may contain standard nucleotides [e.g. standard DNA deoxyribonucleotides (deoxyadenosine monophosphate, deoxyguanosine monophosphate, thymidine monophosphate, deoxycytidine monophosphate) or standard RNA ribonucleotides (adenosine monophosphate, guanosine monophosphate, uridine monophosphate, cytidine monophosphate)], alternative nucleotides (e.g. inosine), modified nucleotides, nucleotide analogs, or a combination thereof. For example, an oligonucleotide primer may include peptide nucleic acids, morpholinos (e.g. phosphorodiamidate morpholino oligos), locked nucleic acids [see, for example, Kaur, H, et. al, Biochemistry 45 (23), 7347-55 (2006)], glycol nucleic acids, or threose nucleic acids. A primer may have a backbone, including, for example, phosphodiester linkages, phosphorothioate linkages (a non-bridging O is replaced with sulfur), or peptide linkages (as part of a peptide nucleic acid). Alternative nucleotides, modified nucleotides, and nucleotide analogs may be referred to collectively herein as "non-standard nucleotides."

The presence of a non-standard nucleotide in a primer may affect various properties of the primer. In some embodiments, inclusion of a non-standard nucleotide in a primer may increase or decrease the thermodynamic stability of a primer to a complementary sequence thereof. For example, a primer having increased thermodynamic stability may contain a locked nucleic acid. A primer having decreased thermodynamic stability may contain, for example, inosine (described by Auer et al., Nucl. Acids Res. 24; 5021-5025 (1996)) or a negatively charged chemical group, such as a carboxylic acid.

A primer provided herein may be of any length. In some embodiments, a primer may be at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 500, 750, 1000, or 1500 nucleotides in length. In some embodiments, a primer may be no more than 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 500, 750, 1000, or 1500 nucleotides in length. In some embodiments, a primer may have a length selected from a range having a minimum value of 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 500, 750, or 1000 nucleotides in length, and a maximum value of 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 500, 750, 1000, or 1500 nucleotides in length.

In some embodiments, a primer may be of any length and contain any nucleotide sequence which permits sufficiently stable and specific annealing of the primer to its complement at the temperature being used for a method or step thereof involving the primer. The exact length desired of a primer may depend on a variety of factors, including the temperature of a reaction, the chemical composition of the primer, and the reaction involving the primer. In some embodiments, the template-binding region of a primer may be of any length and contain any nucleotide sequence which permits sufficiently stable and specific annealing of the template-binding region of the primer to its complement at the temperature being used for a method or step thereof involving the primer. The exact length desired of the template-binding region of a primer may depend on a variety of factors, including the temperature of a reaction, the chemical composition of the template-binding region of the primer, and the reaction involving the primer. The inclusion of one or more non-standard nucleotides in the primer may change the desired length of the primer for use in a method provided herein, as compared to the length of a corresponding primer lacking a non-standard nucleotide. For example, if with a method provided herein it is desired to have a primer with a certain Tm, in some embodiments, a primer with the selected Tm may be of a shorter length if the primer contains at least some non-standard nucleotides, as compared to if the primer contains only standard nucleotides.

A primer provided herein may be prepared by any suitable method. For example, a primer may be chemically synthesized. In another example, a naturally occurring nucleic acid may be isolated, cleaved (e.g. with restriction enzymes), and/or modified to generate or to become part of a primer described herein.

In some embodiments, a label may be attached to a primer. Labels include, for example, binding ligands (e.g. digoxin or biotin), enzymes, fluorescent molecules/fluorophores, luminescent molecules, quencher molecules, or radioisotopes. In other embodiments, a base of an oligonucleotide may be replaced with a fluorescent analog, such as 2-aminopurine (see, for example, Proc. Acad. Sci. USA, 91, 6644-6648 (1994), which is herein incorporated by reference in its entirety).

In some embodiments, conditions such that: i) a primer anneals to a template strand in a primer-based replication process provided herein, or ii) a 3' terminal region of a first strand of a first multiple template linear double-stranded nucleic acid anneals with a 3' terminal region of a second strand of a second multiple template linear double-stranded nucleic acid, to produce a cross-over structure comprising these strands, may each include incubating the nucleic acids at a temperature such that the strands of double-stranded nucleic acid molecules "breathe" (i.e. undergo brief periods of localized rupture of hydrogen bonds connecting base pairs) to a degree sufficient to facilitate the entry of a primer or different nucleic acid strand between the strands of a double-stranded molecule, and the annealing of the primer or different nucleic acid strand to one of the strands of the opened double-stranded nucleic acid molecule. In some embodiments, methods or processes provided herein may be performed or incubated at a temperature of at least 10, 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, or 95 C. In some embodiments, methods or processes provided herein may be performed or incubated at a temperature of no greater than 10, 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, or 95 C. In some embodiments, methods or processes provided herein may be performed or incubated at a temperature between 10, 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, or 90 C and 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90 or 95 C.

In some embodiments, for a method or process provided herein, the step or process is performed at a temperature below the melting temperature (Tm) of the relevant potentially paired nucleotide strands, or regions thereof (e.g. a primer to a nucleic acid template strand, or a 3' terminal region of a first strand of a first multiple template linear double-stranded nucleic acid anneals with a 3' terminal region of a second strand of a second multiple template linear double-stranded nucleic acid, etc.) In some embodiments, for a method or process provided herein, the process or method is performed at a temperature above the Tm of the relevant potentially paired nucleotide strands, or regions thereof. Generally, "melting temperature" of a nucleotide sequence refers to the temperature at which 50% of nucleic acids having the nucleotide sequence are based paired to a complementary sequence thereof (i.e. are in a double-stranded molecule), and 50% of nucleic acids having the nucleotide sequence are in single-stranded form.

In some embodiments, a nucleic acid polymerase is included with a method or composition provided herein. A polymerase may generate an extension product of a primer. The primer and extension product thereof may be complementary to a template nucleic acid strand. Generally, a nucleic acid polymerase will initiate synthesis of an extension product of a primer at the 3' end of the primer. In some embodiments, a DNA polymerase is included with a method or composition provided herein. As used herein, a "DNA polymerase" refers to a nucleic acid polymerase which has primary or exclusive polymerase activity on DNA templates. In some embodiments, a reverse transcriptase is included with a method or composition provided herein. As used herein, a "reverse transcriptase" refers to a nucleic acid polymerase which can synthesize a DNA strand from an RNA template. In some embodiments, an RNA polymerase may be included with a method or composition provided herein. As used herein, a "RNA polymerase" refers to a nucleic acid polymerase which can synthesize an RNA strand from a DNA or RNA template.

In some embodiments, a polymerase provided herein may have strand displacement activity. Polymerases, having strand displacement activity include, for example, exo-Bca DNA polymerase, phi29 DNA polymerase, Klenow Fragment of *E. coli* DNA Polymerase I, $Vent_R$ DNA polymerase, Deep $Vent_R$ DNA polymerase, 9° $N_m$ DNA polymerase, and Large Fragment of Bst DNA Polymerase. Other polymerases having strand displacement activity may also be used.

Modified versions of polymerases may also be used with the methods and compositions provided herein, provided that the modified polymerase has sequence-dependent nucleic acid synthesis activity. A modified version of a polymerase ("modified polymerase") may have, for example, 100 or fewer, 70 or fewer, 50 or fewer, 40 or fewer, 30 or fewer, 20 or fewer, 10 or fewer, 5 or fewer, 4 or fewer, 3 or fewer, 2 or fewer, or 1 different amino acid from the sequence of the parent version of the polymerase. In some embodiments, a modified polymerase may contain no more than 1000, 700, 500, 400, 300, 200, 100, 50, 40, 30, 20, 10, or 5 greater or fewer amino acids than the parent polymerase. In some embodiments, a modified polymerase may comprise a fragment of a parent polymerase. In some embodiments, a modified polymerase may comprise a chimeric polypeptide with a portion derived from a polymerase and a portion derived from a non-polymerase protein. In some embodiments, a modified polymerase may have, for example, increased catalytic activity, increased stability, or increased thermostability as compared to the parent polymerase.

In some embodiments, a polymerase provided herein is thermostable. A thermostable polymerase may have, for example, a half-life of at least 5, 10, 15, 20, 30, 40, 50, 60, 90, 120, or 180 minutes at a temperature of at up to 25, 30, 35 40, 45, 50, 55, 60, 65, 70, 75, 80, 85, 90, or 95 C. In some embodiments, a modified polymerase may be thermostable.

In some embodiments, methods and processes provided herein include or are performed under conditions sufficient to support polymerase-based nucleic acid synthesis. Example conditions for polymerase-based nucleic acid synthesis are known in the art and are provided, for example, in Green and Sambrook, supra. Non-limiting components for a polymerase-based nucleic acid synthesis reaction may include one or more of: polymerase enzyme (at a concentration between, for example, 0.01 and 10 units enzyme per 50 microliters reaction volume, or any range therein including, for example, between 0.01-1, 0.1-10, 0.1-5, 0.5-10, 0.5-5, 0.5-2, 1-10, or 1-5 units enzyme per 50 microliters reaction volume, where 1 unit of enzyme will incorporate 15 nmol of dNTPs into polymerization product in 30 minutes at 75 C); template (at a concentration of at least, for example, 1, 10, 100, 1,000, 10,000, or 100,000 copies per reaction); primer (at a concentration between, for example, 0.01 and 10 micromolar, or any range therein including, for example, between 0.01-1, 0.1-10, 0.1-5, 0.5-5, or 0.5-2 micromolar); dNTPs (e.g. dATP, dTTP, dGTP, and dCTP, at a concentration between, for example, 50 and 500 micromolar each of dATP, dTTP, dGTP, and dCTP, or any range therein including, for example, between 50-350, 100-500, 100-300, 200-500, or 300-400 micromolar each of dATP, dTTP, dGTP, and dCTP); salt (e.g. KCl or potassium acetate, at a concentration between, for example, 1 and 200 millimolar, or any range therein including, for example, between 1-100, 1-50, 1-20, 1-10, 10-20, 10-50, or 10-200 millimolar); buffer (e.g. Tris-HCl or Tris-acetate, pH 7.8-8.5, at a concentration between, for example, 1 and 100 millimolar, or any range therein including, for example, between 1-50, 1-20, 1-10, 1-5, 10-100, 20-100, or 50-100 millimolar); and magnesium ions (at a concentration between, for example 0.1 and 10 millimolar, or any range therein, including, for example, between 0.1-5, 0.1-1, 0.5-10, 0.5-5, or 0.5-2.5 millimolar). Additional non-limiting components for a polymerase-based nucleic acid synthesis reaction may increase the speed of the reaction, increase the fidelity of the reaction, or increase the stability of enzymes or DNA in the reaction, and may include one or more of: gelatin (at a concentration between, for example, 0.0001% and 0.1% w/v), BSA (at a concentration between, for example, 0.01 and 1 microgram per microliter), sucrose (at a concentration between, for example 0.01 molar and 0.8 molar), trehalose (at a concentration between, for example 0.01 molar and 0.8 molar), DMSO (at a concentration between, for example, 0.01 and 10% v/v), betaine (at a concentration between, for example, 0.1 and 10 molar), formamide (at a concentration between, for example, 0.1 and 10% v/v), glycerol (at a concentration between, for example, 0.1 and 20% v/v), polyethylene glycol (at a concentration between, for example, 0.1 and 20% v/v), non-ionic detergents [e.g. NP-40 (at a concentration between, for example, 0.01 and 1% v/v), Tween-20 (at a concentration between, for example, 0.01 and 1% v/v), or Triton X-100 (at a concentration between, for example, 0.01 and 1% v/v)], ammonium ions [e.g. ammonium sulfate (at a concentration between, for example, 1 and 100 millimolar)], and EDTA (at a concentration between, for example, 0.001 and 0.1 millimolar). Other reagents may also be present in a polymerase-based nucleic acid synthesis reaction provided herein. For example, reagents to sufficient to synthesize RNA reaction products or reaction products containing non-standard nucleotides may be used. Conditions sufficient to support polymerase-based nucleic acid synthesis may include a variety of temperatures and pH values. For example, the pH of a of a polymerase-based nucleic acid synthesis reaction be between, for example pH 6.0 and pH 10.0, such as 6.5, 7, 7.5, 7.8, 7.9, 8, 8.1, 8.2, 8.5, 9, or 9.5. The temperature of a polymerase-based nucleic acid synthesis reaction may be constant or varied. A constant temperature may be between, for example, 10 C and 95 C, such as 20, 25, 30, 35, 37, 40, 42, 45, 50, 55, 60, 65, 70, 75, 80, or 85 C. A varied temperature may at two or more different temperatures between, for example 10 C and 95 C, such two or more temperatures selected from 20, 25, 30, 35, 37, 40, 42, 45, 50, 55, 60, 65, 70, 75, 80, or 85 C.

In some embodiments, a nucleic acid ligase is included with a method or composition provided herein. Ligases catalyze the formation of phosphodiester bonds between nucleotides, typically between the 5' phosphate of one nucleotide, and the 3' hydroxyl group of another nucleotide.

Nucleic acid ligases include *E. coli* DNA ligase, Taq DNA ligase, T3 DNA ligase, T4 DNA ligase, T7 DNA ligase, Ampligase™, T4 RNA ligase 1, and T4 RNA ligase 2.

In order to catalyze the ligation reaction, certain ligases require ATP (e.g. T4 DNA ligase) or NAD+ (*E. coli* DNA ligase). In some embodiments, a ligase may ligate nucleic acids having blunt ends. In some embodiments, a ligase may ligate nucleic acids having sticky ends. In some embodiments, a ligase may ligate nucleic acids having both blunt and sticky ends.

Modified versions of ligases may also be used with the methods and compositions provided herein, provided that the modified ligase has the ability to catalyze the formation of phosphodiester bonds between nucleotides. A modified version of a ligase ("modified ligase") may have, for example, 100 or fewer, 70 or fewer, 50 or fewer, 40 or fewer, 30 or fewer, 20 or fewer, 10 or fewer, 5 or fewer, 4 or fewer, 3 or fewer, 2 or fewer, or 1 different amino acid from the sequence of the parent, naturally occurring version of the ligase. In some embodiments, a modified ligase may contain no more than 1000, 700, 500, 400, 300, 200, 100, 50, 40, 30, 20, 10, or 5 greater or fewer amino acids than the parent ligase. In some embodiments, a modified ligase may comprise a fragment of a parent ligase. In some embodiments, a modified ligase may comprise a chimeric polypeptide with a portion derived from a ligase and a portion derived from a non-ligase protein. In some embodiments, a modified ligase may have, for example, increased catalytic activity, increased stability, or increased thermostability as compared to the parent ligase.

In some embodiments, a ligase provided herein is thermostable. A thermostable ligase may have, for example, a half-life of at least 5, 10, 15, 20, 30, 40, 50, 60, 90, 120, or 180 minutes at a temperature of at up to 25, 30, 35 40, 45, 50, 55, 60, 65, 70, 75, 80, 85, 90, or 95 C. In some embodiments, a modified ligase may be thermostable.

In some embodiments, a ligase used with methods and compositions provided herein may be a modified ligase referred to herein as "p50-Tth", which has the amino acid sequence:

(SEQ ID NO: 1)
MGHHHHHHHHHHSSGHIEGRAS*ADGPYLQILEQPKQRGFRFRYVCEGPSH*
*GGLPGASSEKNKKSYPQVKICNYVGPAKVIVQLVTNGKNIHLHAHSLVGK*
*HCEDGICTVTAGPKDMVVGFANLGILHVTKKKVFETLEARMTEACIRGYN*
*PGLLVHPDLAYLQAEGGGDRQLGDREKELIRQAALQQTKEMDLSVVRLMF*
*TAFLPDSTGSFTRRLEPVVSDAIYDSKAPNASNLKIVRMDRTAGCVTGGE*
*EIYLLCDKVQKDDIQIRFYEEEENGGVWEGFGDFSPTDVHRQFAIVFKTP*
*KYKDINITKPASVFVQLRRKSDLETSEPKPFLYYPEIKDKEEVQRKRQK*G
SSGTSGGGSGGGMTLEEARKRVNELRDLIRYHNYRYYVLADPEISDAEYD
RLLRELKELEERFPELKSPDSPTLQVGARPLEATFRPVRHPTRMYSLDNA
FNLDELKAFEERIERALGRKGPFAYTVEHKVDGLSVNLYYEEGVLVYGAT
RGDGEVGEEVTQNLLTIPTIPRRLKGVPERLEVRGEVYMPIEAFLRLNEE
LEERGERIFKNPRNAAAGSLRQKDPRITAKRGLRATFYALGLGLEEVERE
GVATQFALLHWLKEKGFPVEHGYARAVGAEGVEAVYQDWLKKRRALPFEA
DGVVVKLDELALWRELGYTARAPRFAIAYKFPAEEKETRLLDVVFQVGRT
GRVTPVGILEPVFLEGSEVSRVTLHNESYIEELDIRIGDWVLVHKAGGVI
PEVLRVLKERRTGEERPIRWPETCPECGHRLLKEGKVHRCPNPLCPAKRF
EAIRHFASRKAMDIQGLGEKLIERLLEKGLVKDVADLYRLRKEDLVGLER
MGEKSAQNLLRQTEESKKRGLERLLYALGLPGVGEVLARNLAARFGNMDR
LLEASLEELLEVEEVGELTARAILETLKDPAFRDLVRRLKEAGVEMEAKE
KGGEALKGLTFVITGELSRPREEVKALLRRLGAKVTDSVSRKTSYLVVGE
NPGSKLEKARALGVPTLTEEELYRLLEARTGKKAEELV.

Ligase p50-Tth has thermostable blunt-end ligation activity at temperatures of at least 60 C. Ligase p50-Tth is a chimeric protein which comprises a His10-containing leader sequence, a p50 sequence from the human NF-kappa-B protein accession number NP_003989 amino acids 40-366 (indicated in italics), a flexible glycine rich sequence, and a Tth DNA ligase sequence, from *Thermus Thermophilus* HB8, accession YP_144363 (indicated with underlining). In some embodiments, a modified version of p50-Tth ligase may be used with methods and compositions provided herein (e.g. with 100 or fewer, 70 or fewer, 50 or fewer, 40 or fewer, 30 or fewer, 20 or fewer, 10 or fewer, 5 or fewer, 4 or fewer, 3 or fewer, 2 or fewer, or 1 different amino acids from p50-Tth ligase). In embodiments, a ligase used with a composition or method provided herein may be a ligase described in U.S. Provisional Patent Application No. 61/802,124, filed Mar. 15, 2013 or PCT Application No. PCT/US14/30003, filed Mar. 15, 2014, both of which are herein incorporated by reference in their entirety for all purposes.

Methods provided herein may be performed at a variety of temperatures. In some embodiments, all steps of a method are performed at the same temperature. Thus, temperature cycling such as in PCR is not necessary with methods disclosed herein. In some embodiments, methods provided herein may be performed at two or more different temperatures. In some embodiments, a reaction mixture containing reagents for a method provided herein is incubated at two or more different temperatures. In some examples, different temperatures may be selected to optimize the rate, accuracy, or other feature of different processes of a method provided herein. For example, a temperature may be selected to increase the enzymatic activity of a polymerase. In some examples, different temperatures may be selected to increase the binding specificity of a primer to a template or to increase the accessibility of a template to a primer (e.g. higher temperatures may promote the separation of duplex template nucleic acids, or may promote the sequence-specific binding of primers). In some embodiments, all of the steps of a method provided herein are performed at a temperature of no greater than 80, 70, 60, 50, 40, 30, 20 or 10° C. In some embodiments, a method provided herein is performed at a temperature between 20-60, 30-70, 40-80, 30-40, 35-45, 40-50, 45-55, 50-60, or 55-65° C. In certain embodiments, a sample containing a target nucleic acid may be heated to a temperature greater than 40, 50, 60, 70, 80, 90, or 95 C before the initiation of a method provided herein. In certain embodiments, a reaction mixture provided herein may be heated one time to an elevated temperature greater than 40, 50, 60, 70, 75, 80, 85, 90, or 95 C before or after the initiation of a method provided herein. After heating the reaction mixture to the elevated temperature, it may be maintained at a lower temperature as provided elsewhere herein (e.g. at a temperature between 40-70 C) for the remainder of the performance of the method. In embodiments, if a reaction mixture or sample is heated to an elevated temperature before the initiation of a method provided herein, a nucleic acid polymerase may be added to the reaction mixture or sample after the reaction mixture or sample has been heated to the elevated temperature, and the reaction mixture or sample has been returned to a lower temperature as provided herein. Methods disclosed herein may be performed with or without a thermocycler.

As one consideration, the temperature used for a method or process provided herein may be selected to be appropriate for the enzyme(s) being used in the method. In some embodiments, for methods in which a polymerase or ligase is used, the temperature(s) of the reaction is selected such that it does not significantly impair the activity of the polymerase or ligase (e.g. the temperature of the reaction may be selected such that polymerase and ligase have a half-life of at least 24, 12, 6, 4, 3, 2, 1, 0.75, 0.5, 0.25, or 0.1 hours). Alternatively, methods may be performed at a temperature that impairs the activity of the enzyme(s) being used in the method (e.g. the temperature of the reaction may be selected such that an enzyme in the reaction has a half-life of no more than 24, 12, 6, 4, 3, 2, 1, 0.75, 0.5, 0.25, or 0.1 hours). In some embodiments, if a method is performed at a temperature or other condition (e.g. pH) that impairs the activity of one or more the enzymes, additional enzyme may be added to the reaction at one or more intervals after the initiation of the method to supplement the activity of the impaired enzyme(s).

In some embodiments, one or more processes of a method provided herein occur in the same reaction vessel (e.g. tube, tip, container, etc.). In some embodiments, all of the processes of a method occur in the same reaction vessel.

Reagents for methods provided herein can all be provided together at the start of a reaction, or they may be added sequentially, where after one, two, or more steps new reagents are added to a reaction. In some circumstances, new reagents (e.g. enzymes, primers) may be added to a reaction vessel during the course of the reaction, to increase the amount of reagents available to act on substrates or to replace the function of reagents that have become inactivated (e.g. enzymes). New reagents may be added to a reaction at one or more selected time intervals after the initiation of a reaction of a method provided herein (for example, at 1, 3, 5, 7, 10, 15, 20, 30, 45, or 60 minutes after the initiation of a reaction).

In some embodiments, two or more sets of first and second primers are provided in a method provided herein, where each set contains a first primer and a second primer, and where different primer sets are complementary to different nucleic acid templates. Both the first and second primers in a set are complementary to different strands of the same nucleic acid template. Inclusion of two or more primer sets in a method provided herein may support the simultaneous amplification of multiple different nucleic acid templates in the same reaction vessel. This may be useful, for example, for amplifying multiple templates of interest in a sample, or for assaying for the presence of multiple different templates in a sample. In some embodiments, 1, 2, 3, 4, 5, 6, 7, 8, 9, 10, 15, 20, 25, 30, 40, 50, 60, 70, 100, 200, 500 or more sets of first and second primers are provided in a method provided herein, in order to amplify or assay for the presence of 1, 2, 3, 4, 5, 6, 7, 8, 9, 10, 15, 20, 25, 30, 40, 50, 60, 70, 100, 200, 500 or more different nucleic acid templates.

In some embodiments, provided herein is a vessel containing one or more enzymes, primers, or other reagents provided herein. Vessels may include any structure capable of supporting or containing a liquid or solid material and may include, tubes, containers, tips, etc. In some embodiments, a wall of a vessel may permit the transmission of light through the wall. A vessel may be optically clear. A vessel may contain, for example, any one or more of an isolated nucleic acid polymerase, an isolated DNA polymerase, an isolated reverse transcriptase, an isolated ligase, a first primer, a second primer, a nucleic acid dye, or a nucleic acid probe, as described elsewhere herein. Any number of copies of any of the contents of a vessel may be provided (e.g. a first copy, a second copy, a third copy, etc.) The contents of a vessel may be in fluid communication. In some embodiments, a vessel may further contain a nucleic acid template. In some embodiments, a vessel may further contain nucleotides, buffers, salts, water, or other reagents provided herein for the amplification of nucleic acids. In some embodiments, a vessel may contain two or more sets of primers, wherein each primer set comprises a first and second primer, and the different primer sets are complementary to different nucleic acid templates.

Two or more reagents useful for a method provided herein may be packaged and provided as a kit. For example, a kit may include any two or more of: a nucleic acid template, a first primer, a second primer, a nucleic acid polymerase, a DNA polymerase, a reverse transcriptase, an isolated ligase, buffers, a nucleic acid dyes, a nucleic acid probe, or dNTPs, as described elsewhere herein. Within the kit, the two or more reagents may be packaged in separate vessels or the same vessel. In some embodiments, a kit may further contain nucleotides, buffers, salts, water, or other reagents provided herein for the amplification of nucleic acids.

The various methods and compositions provided herein for the amplification of a nucleic acid template can fulfill many of the functions that have previously been carried out by other methods and compositions for isothermal and thermocycler-dependent nucleic acid amplification. A nucleic acid template for amplification according to methods provided herein may also be referred to herein as a "target nucleic acid" or the like. Methods and compositions provided herein may be used, for example, for isolation and cloning of nucleic acids of interest, gene expression analysis, diagnostic identification of nucleic acids, synthesis of novel nucleic acids, nucleic acid probe synthesis and labeling, forensic identification of a subject, allele identification from a subject, genetic screening, nucleic acid sequencing, and related applications. A target nucleic acid molecule may be of any type, including single-stranded or double stranded and DNA or RNA (e.g. mRNA). A target nucleic acid may be of any type or function (e.g. a protein-coding sequence, a regulatory sequence, an intron, etc.). A target nucleic acid may be the entirety of a gene, or a portion thereof. Methods provided herein may include conversion of a single strand nucleic acid target molecule to a template linear double-stranded nucleic acid by methods disclosed herein or otherwise known in the art.

In some embodiments, a method or composition provided herein may be used to detect the amount of a target nucleic acid in a sample (including the presence or absence of the target), to measure the amount of an amplification product of a target formed from a sample in a selected period of time, or to determine the amount of time necessary to generate a certain number of copies of a template from a sample. Samples which may be used with methods and compositions provided herein are described elsewhere herein, and may include, for example, a bodily fluid, a secretion, or a tissue of a subject. In embodiments, a sample may be processed prior to use of the sample in an assay to amplify a target nucleic acid in the sample according to a method provided herein. Processing of the sample may include any processing step as described elsewhere herein, and may include, for example, sonication or chemical lysing steps.

In some embodiments, a method provided herein may be performed to simultaneously assay for at least 2, 3, 4, 5, 6, 7, 8, 9, 10, 12, 15, 20, 25, 30, 35, 40, 45, 50, 75, 100, or more different target nucleic acids in the same reaction vessel. Typically, for each target nucleic acid of interest, a first primer and a second primer are provided, each being complementary to a strand of the nucleic acid target, or a complement thereof. The amplification of the different target nucleic acids in the same vessel may be monitored, for example, by the use of nucleic acid probes having sequence specificity for detection sequences in the different target nucleic acids, and different fluorophores.

In some embodiments, a method or composition provided herein may be used to detect the presence or absence of a particular nucleotide of interest in a target nucleic acid (e.g. in the case of a mutation or SNP). For example, a first or second primer may be selected which selectively binds to a region in a target nucleic acid which includes or is adjacent to the nucleotide of interest. The primer may be designed such that it selectively either: i) binds to the region when the region contains the nucleotide of interest, or ii) does not bind to the region when the region contains the nucleotide of interest. A method as described herein may be performed with the selected primer, and the outcome of the amplification reaction may provide information regarding the presence or absence of the nucleotide of interest in the target nucleic acid. For example, if a first primer is designed to have a nucleotide sequence which is complementary to a sequence in the target nucleic acid which includes a particular nucleotide of interest (e.g. a mutation), successful amplification of the target nucleic acid with the selected primer from a sample may indicate that the sample contains a target nucleic acid having the particular nucleotide of interest. In some embodiments, a primer used for analysis of a nucleotide of interest in a target nucleic acid may contain a critical nucleotide at the 3' terminus of the primer (i.e. a nucleotide which corresponds to the same position of a nucleotide of interest in the target nucleic acid). In such a case, the annealing of the 3' terminal nucleotide of the primer may be dependent on the presence of the nucleotide of interest in the target nucleic acid. If the 3' terminal nucleotide of the primer does not anneal with a nucleotide in the target nucleic acid (e.g. due to a mismatch between the nucleotides), the mismatch may significantly impair a nucleic acid polymerase from synthesizing an extension product from the primer. Accordingly, in some embodiments, a primer having a 3' terminal nucleotide which corresponds to a nucleotide of interest may be useful for determining the presence or absence of a particular nucleotide in a target nucleic acid. In such embodiments, in some situations the critical nucleotide at the 3' terminus of the primer may be selected to be complementary the nucleotide of interest in the target nucleic acid, and in some other situations the critical nucleotide at the 3' terminus of the primer may be selected to be non-complementary the nucleotide of interest in the target nucleic acid. The nucleotide of interest may represent, for example, a wild-type form, a mutant form, or a polymorphism of a target nucleic acid.

Methods and compositions provided herein may be used to amplify a nucleic acid from any sample which may contain nucleic acids. Examples of samples may include various fluid samples. In some instances, the sample may be a bodily fluid sample from a subject. The sample may include one or more fluid component. In some instances, solid or semi-solid samples may be provided. The sample may include tissue collected from the subject. The sample may include a bodily fluid, secretion, or tissue of a subject. The sample may be a biological sample. The biological sample may be a bodily fluid, a secretion, or a tissue sample. Examples of biological samples may include but are not limited to, blood, serum, saliva, urine, gastric and digestive fluid, tears, stool, semen, vaginal fluid, interstitial fluids derived from tumorous tissue, ocular fluids, sweat, mucus, earwax, oil, glandular secretions, breath, spinal fluid, hair, fingernails, skin cells, plasma, nasal swab or nasopharyngeal wash, spinal fluid, cerebral spinal fluid, tissue, throat swab, biopsy, placental fluid, amniotic fluid, cord blood, emphatic fluids, cavity fluids, sputum, pus, microbiota, meconium, breast milk or other excretions. The sample may be provided from a human or animal. Samples may be from a plant, microorganism (e.g. virus, bacteria), or other biological material.

In some embodiments, methods and compositions provided herein may be performed at or used at point of service locations (e.g. a subject's home or work, grocery stores, drug stores, clinics, schools, etc.). Methods and compositions provided herein may permit the rapid amplification of nucleic acids in a sample from a subject, in order to aid in the diagnosis or treatment of a subject. For example, methods and compositions provided here may be used test a sample from a subject for the presence of nucleic acid from a pathogen, such a virus (e.g. influenza) or bacteria (e.g. *streptococcus*).

The assays and methods disclosed herein may be performed on a device, or on a system, for processing a sample. The assays and methods disclosed herein can be readily incorporated into and used in device for processing a sample, or a system for processing a sample, which may be an automated assay device, or may be an automated assay system. Such a device, and such a system, may be useful for the practice of the methods disclosed herein. For example, a device may be useful for receiving a sample. A device may be useful for preparing, or for processing a sample. A device may be useful for performing an assay on a sample. A device may be useful for obtaining data from a sample. A device may be useful for transmitting data obtained from a sample. A device may be useful for disposing of a sample following processing or assaying of a sample.

A device may be part of a system, a component of which may be a sample processing device. A device may be a sample processing device. A sample processing device may be configured to facilitate collection of a sample, prepare a sample for a clinical test, or perform a method with one or more reagents, as disclosed herein. A sample processing device may be configured to obtain data from a sample. A sample processing device may be configured to transmit data obtained from a sample. A sample processing device may be configured to analyze data from a sample. A sample processing device may be configured to communicate with another device, or a laboratory, or an individual affiliated with a laboratory, to analyze data obtained from a sample.

A sample processing device may be configured to be placed in or on a subject. A sample processing device may be configured to accept a sample from a subject, either directly or indirectly. A sample may be, for example, a blood sample (e.g., a sample obtained from a fingerstick, or from venipuncture, or an arterial blood sample), a urine sample, a biopsy sample, a tissue slice, stool sample, or other biological sample; a water sample, a soil sample, a food sample, an air sample; or other sample. A blood sample may comprise, e.g., whole blood, plasma, or serum. A sample processing device may receive a sample from the subject through a housing of the device. The sample collection may occur at a sample collection site, or elsewhere. The sample may be provided to the device at a sample collection site.

In some embodiments, a sample processing device may be configured to accept or hold a cartridge. In some embodiments, a sample processing device may comprise a cartridge. The cartridge may be removable from the sample processing device. In some embodiments, a sample may be provided to the cartridge of the sample processing device. Alternatively, a sample may be provided to another portion of a sample processing device. The cartridge and/or device may comprise a sample collection unit that may be configured to accept a sample.

A cartridge may include a sample, and may include reagents for use in processing or testing a sample, disposables for use in processing or testing a sample, or other materials. A cartridge may contain reagents disclosed herein for the performing a method disclosed herein. Following placement of a cartridge on, or insertion of a cartridge into, a sample processing device, one or more components of the cartridge may be brought into fluid communication with other components of the sample processing device. For example, if a sample is collected at a cartridge, the sample may be transferred to other portions of the sample processing device. Similarly, if one or more reagents are provided on a cartridge, the reagents may be transferred to other portions of the sample processing device, or other components of the sample processing device may be brought to the reagents. In some embodiments, the reagents or components of a cartridge may remain on-board the cartridge. In some embodiments, no fluidics are included that require tubing or that require maintenance (e.g., manual or automated maintenance).

A sample or reagent may be transferred to a device, such as a sample processing device. A sample or reagent may be transferred within a device. Such transfer of sample or reagent may be accomplished without providing a continuous fluid pathway from cartridge to device. Such transfer of sample or reagent may be accomplished without providing a continuous fluid pathway within a device. In embodiments, such transfer of sample or reagent may be accomplished by a sample handling system (e.g., a pipette); for example, a sample, reagent, or aliquot thereof may be aspirated into an open-tipped transfer component, such as a pipette tip, which may be operably connected to a sample handling system which transfers the tip, with the sample, reagent, or aliquot thereof contained within the tip, to a location on or within the sample processing device. The sample, reagent, or aliquot thereof can be deposited at a location on or within the sample processing device. Sample and reagent, or multiple reagents, may be mixed using a sample handling system in a similar manner. One or more components of the cartridge may be transferred in an automated fashion to other portions of the sample processing device, and vice versa.

A device, such as a sample processing device, may have a fluid handling system. A fluid handling system may perform, or may aid in performing, transport, dilution, extraction, aliquotting, mixing, and other actions with a fluid, such as a sample. In some embodiments, a fluid handling system may be contained within a device housing. A fluid handling system may permit the collection, delivery, processing and/or transport of a fluid, dissolution of dry reagents, mixing of liquid and/or dry reagents with a liquid, as well as collection, delivery, processing and/or transport of non-fluidic components, samples, or materials. The fluid may be a sample, a reagent, diluent, wash, dye, or any other fluid that may be used by the device, and may include, but not limited to, homogenous fluids, different liquids, emulsions, suspensions, and other fluids. A fluid handling system, including without limitation a pipette, may also be used to transport vessels (with or without fluid contained therein) around the device. The fluid handling system may dispense or aspirate a fluid. The sample may include one or more particulate or solid matter floating within a fluid.

In embodiments, a fluid handling system may comprise a pipette, pipette tip, syringe, capillary, or other component. The fluid handling system may have portion with an interior surface and an exterior surface and an open end. The fluid handling system may comprise a pipette, which may include a pipette body and a pipette nozzle, and may comprise a pipette tip. A pipette tip may or may not be removable from a pipette nozzle. In embodiments, a fluid handling system may use a pipette mated with a pipette tip; a pipette tip may be disposable. A tip may form a fluid-tight seal when mated with a pipette. A pipette tip may be used once, twice, or more times. In embodiments, a fluid handling system may use a pipette or similar device, with or without a pipette tip, to aspirate, dispense, mix, transport, or otherwise handle the fluid. The fluid may be dispensed from the fluid handling system when desired. The fluid may be contained within a pipette tip prior to being dispensed, e.g., from an orifice in the pipette tip. In embodiments, or instances during use, all of the fluid may be dispensed; in other embodiments, or instances during use, a portion of the fluid within a tip may be dispensed. A pipette may selectively aspirate a fluid. The pipette may aspirate a selected amount of fluid. The pipette may be capable of actuating stirring mechanisms to mix the fluid within the tip or within a vessel. The pipette may incorporate tips or vessels creating continuous flow loops for mixing, including of materials or reagents that are in non-liquid form. A pipette tip may also facilitate mixture by metered delivery of multiple fluids simultaneously or in sequence, such as in 2-part substrate reactions.

The fluid handling system may include one or more fluidically isolated or hydraulically independent units. For example, the fluid handling system may include one, two, or more pipette tips. The pipette tips may be configured to accept and confine a fluid. The tips may be fluidically isolated from or hydraulically independent of one another. The fluid contained within each tip may be fluidically isolated or hydraulically independent from one fluids in other tips and from other fluids within the device. The fluidically isolated or hydraulically independent units may be movable relative to other portions of the device and/or one another. The fluidically isolated or hydraulically independent units may be individually movable. A fluid handling system may comprise one or more base or support. A base or support may support one or more pipette or pipette units. A base or support may connect one or more pipettes of the fluid handling system to one another.

A sample processing device may be configured to perform processing steps or actions on a sample obtained from a subject. Sample processing may include sample preparation, including, e.g., sample dilution, division of a sample into aliquots, extraction, contact with a reagent, filtration, separation, centrifugation, or other preparatory or processing action or step. A sample processing device may be configured to perform one or more sample preparation action or step on the sample. Optionally, a sample may be prepared for a chemical reaction and/or physical processing step. A sample preparation action or step may include one or more of the following: centrifugation, separation, filtration, dilution, enriching, purification, precipitation, incubation, pipetting, transport, chromatography, cell lysis, cytometry, pulverization, grinding, activation, ultrasonication, micro column processing, processing with magnetic beads, processing with nanoparticles, or other sample preparation action or steps. For example, sample preparation may include one or more step to separate blood into serum and/or particulate fractions, or to separate any other sample into various components. Sample preparation may include one or more step to dilute and/or concentrate a sample, such as a blood sample, or other biological samples. Sample preparation may include adding an anti-coagulant or other ingredients to a sample. Sample preparation may also include purification of a sample. In embodiments, all sample processing, preparation, or assay actions or steps are performed by a single device. In embodiments, all sample processing, preparation, or assay actions or steps are performed within a housing of a single device. In embodiments, most sample processing, preparation, or assay actions or steps are performed by a single device, and may be performed within a housing of a single device. In embodiments, many sample processing, preparation, or assay actions or steps are performed by a single device, and may be performed within a housing of a single device. In embodiments, sample processing, preparation, or assay actions or steps may be performed by more than one device.

A sample processing device may be configured to run one or more assays on a sample, and to obtain data from the sample. A sample processing device may perform methods provided herein, as well as additional assays. An assay may include one or more physical or chemical treatments, and may include running one or more chemical or physical reactions. A sample processing device may be configured to perform one, two or more assays on a small sample of bodily fluid. One or more chemical reaction may take place on a sample having a volume, as described elsewhere herein. For example one or more chemical reaction may take place in a pill having less than femtoliter volumes. In an instance, the sample collection unit is configured to receive a volume of the bodily fluid sample equivalent to a single drop or less of blood or interstitial fluid. In embodiments, the volume of a sample may be a small volume, where a small volume may be a volume that is less than about 1000 μL, or less than about 500 μL, or less than about 250 μL, or less than about 150 μL, or less than about 100 μL, or less than about 75 μL, or less than about 50 μL, or less than about 40 μL, or less than about 20 μL, or less than about 10 μL, less than about 5 μL, less than about 1 μL, less than about 0.5 μL, less than about 0.1 μL, or other small volume. In embodiments, all sample assay actions or steps are performed on a single sample. In embodiments, all sample assay actions or steps are performed by a single device. In embodiments, all sample assay actions or steps are performed within a housing of a single device. In embodiments, most sample assay actions or steps are performed by a single device, and may be performed within a housing of a single device. In embodiments, many sample assay actions or steps are performed by a single device, and may be performed within a housing of a single device. In embodiments, sample processing, preparation, or assay actions or steps may be performed by more than one device.

A sample processing device may be configured to perform a plurality of assays on a sample. In some embodiments, a sample processing device may be configured to perform a method provided herein and one, two, or more additional assays. In embodiments, a sample processing device may be configured to perform a plurality of assays on a single sample. In embodiments, a sample processing device may be configured to perform a plurality of assays on a single sample, where the sample is a small sample. For example, a small sample may have a sample volume that is a small volume of less than about 1000 μL, or less than about 500 μL, or less than about 250 μL, or less than about 150 μL, or less than about 100 μL, or less than about 75 μL, or less than about 50 μL, or less than about 40 μL, or less than about 20 μL, or less than about 10 μL, less than about 5 μL, less than about 1 μL, less than about 0.5 μL, less than about 0.1 μL, or other small volume. A sample processing device may be capable of performing multiplexed assays on a single sample. A plurality of assays may be run simultaneously; may be run sequentially; or some assays may be run simultaneously while others are run sequentially. One or more control assays and/or calibrators (e.g., including a configuration with a control of a calibrator for the assay/tests) can also be incorporated into the device; control assays and assay on calibrators may be performed simultaneously with assays performed on a sample, or may be performed before or after assays performed on a sample, or any combination thereof. In embodiments, all sample assay actions or steps are performed by a single device. In embodiments, all of a plurality of assay actions or steps are performed within a housing of a single device. In embodiments, most sample assay actions or steps, of a plurality of assays, are performed by a single device, and may be performed within a housing of a single device. In embodiments, many sample assay actions or steps, of a plurality of assays, are performed by a single device, and may be performed within a housing of a single device. In embodiments, sample processing, preparation, or assay actions or steps may be performed by more than one device.

In embodiments, all of a plurality of assays may be performed in a short time period. In embodiments, such a short time period comprises less than about three hours, or less than about two hours, or less than about one hour, or less than about 40 minutes, or less than about 30 minutes, or less than about 25 minutes, or less than about 20 minutes, or less than about 15 minutes, or less than about 10 minutes, or less than about 5 minutes, or less than about 4 minutes, or less than about 3 minutes, or less than about 2 minutes, or less than about 1 minute, or other short time period.

A sample processing device may be configured to detect one or more signals relating to the sample. A sample processing device may be configured to identify one or more properties of the sample. For instance, the sample processing device may be configured to detect the presence or concentration of one analyte (e.g. a target nucleic acid) or a plurality of analytes or a disease condition in the sample (e.g., in or through a bodily fluid, secretion, tissue, or other sample). Alternatively, the sample processing device may be configured to detect a signal or signals that may be analyzed to detect the presence or concentration of one or more analytes (which may be indicative of a disease condition) or a disease condition in the sample. The signals may be analyzed on board the device, or at another location. Running a clinical test may or may not include any analysis or comparison of data collected.

A chemical reaction or other processing step may be performed, with or without the sample. Examples of steps, tests, or assays that may be prepared or run by the device may include, but are not limited to immunoassay, nucleic acid assay (e.g. methods provided herein), receptor-based assay, cytometric assay, colorimetric assay, enzymatic assay, electrophoretic assay, electrochemical assay, spectroscopic assay, chromatographic assay, microscopic assay, topographic assay, calorimetric assay, turbidimetric assay, agglutination assay, radioisotope assay, viscometric assay, coagulation assay, clotting time assay, protein synthesis assay, histological assay, culture assay, osmolarity assay, and/or other types of assays, centrifugation, separation, filtration, dilution, enriching, purification, precipitation, pulverization, incubation, pipetting, transport, cell lysis, or other sample preparation action or steps, or combinations thereof. Steps, tests, or assays that may be prepared or run by the device may include imaging, including microscopy, cytometry, and other techniques preparing or utilizing images. Steps, tests, or assays that may be prepared or run by the device may further include an assessment of histology, morphology, kinematics, dynamics, and/or state of a sample, which may include such assessment for cells.

A device may be capable of performing all on-board steps (e.g., steps or actions performed by a single device) in a short amount of time. A device may be capable of performing all on-board steps on a single sample in a short amount of time. For example, from sample collection from a subject to transmitting data and/or to analysis may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less. The amount of time from accepting a sample within the device to transmitting data and/or to analysis from the device regarding such a sample may depend on the type or number of steps, tests, or assays performed on the sample. The amount of time from accepting a sample within the device to transmitting data and/or to analysis from the device regarding such a sample may take about 3 hours or less, 2 hours or less, 1 hour or less, 50 minutes or less, 45 minutes or less, 40 minutes or less, 30 minutes or less, 20 minutes or less, 15 minutes or less, 10 minutes or legs, 5 minutes or less, 4 minutes or less, 3 minutes or less, 2 minutes or less, or 1 minute or less.

A device may be configured to prepare a sample for disposal, or to dispose of a sample, such as a biological sample, following processing or assaying of a sample.

In embodiments, a sample processing device may be configured to transmit data obtained from a sample. In embodiments, a sample processing device may be configured to communicate over a network. A sample processing device may include a communication module that may interface with the network. A sample processing device may be connected to the network via a wired connection or wirelessly. The network may be a local area network (LAN) or a wide area network (WAN) such as the Internet. In some embodiments, the network may be a personal area network. The network may include the cloud. The sample processing device may be connected to the network without requiring an intermediary device, or an intermediary device may be required to connect a sample processing device to a network. A sample processing device may communicate over a network with another device, which may be any type of networked device, including but not limited to a personal computer, server computer, or laptop computer; personal digital assistants (PDAs) such as a Windows CE device; phones such as cellular phones, smartphones (e.g., iPhone, Android, Blackberry, etc.), or location-aware portable phones (such as GPS); a roaming device, such as a network-connected roaming device; a wireless device such as a wireless email device or other device capable of communicating wireless with a computer network; or any other type of network device that may communicate possibly over a network and handle electronic transactions. Such communication may include providing data to a cloud computing infrastructure or any other type of data storage infrastructure which may be accessed by other devices.

A sample processing device may provide data regarding a sample to, e.g., a health care professional, a health care professional location, such as a laboratory, or an affiliate thereof. One or more of a laboratory, health care professional, or subject may have a network device able to receive or access data provided by the sample processing device. A sample processing device may be configured to provide data regarding a sample to a database. A sample processing device may be configured to provide data regarding a sample to an electronic medical records system, to a laboratory information system, to a laboratory automation system, or other system or software. A sample processing device may provide data in the form of a report.

A laboratory, device, or other entity or software may perform analysis on data regarding a sample in real-time. A software system may perform chemical analysis and/or pathological analysis, or these could be distributed amongst combinations of lab, clinical, and specialty or expert personnel. Analysis may include qualitative and/or quantitative evaluation of a sample. Data analysis may include a subsequent qualitative and/or quantitative evaluation of a sample. Optionally, a report may be generated based on raw data, pre-processed data, or analyzed data. Such a report may be prepared so as to maintain confidentiality of the data obtained from the sample, the identity and other information regarding the subject from whom a sample was obtained, analysis of the data, and other confidential information. The report and/or the data may be transmitted to a health care professional. Data obtained by a sample processing device, or analysis of such data, or reports, may be provided to a database, an electronic medical records system, to a laboratory information system, to a laboratory automation system, or other system or software.

Description and disclosure of examples of reagents, assays, methods, kits, devices, and systems which may use, or be used with, methods, compositions, or other reagents disclosed herein may be found, for example, in U.S. Pat. Nos. 8,088,593; 8,380,541; U.S. patent application Ser. No. 13/769,798, filed Feb. 18, 2013; U.S. patent application Ser. No. 13/769,779, filed Feb. 18, 2013; U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; and U.S. Application Ser. No. 61/673,245, filed Sep. 26, 2011, the disclosures of which patents and patent applications are all hereby incorporated by reference in their entireties.

This application claims the benefit of, and priority to U.S. Provisional Patent Application No. 61/802,241, filed Mar. 15, 2013, the disclosure of which is hereby incorporated by reference in its entirety for all purposes.

EXAMPLES

The following examples are offered for illustrative purposes only, and are not intended to limit the present disclosure in any way.

Example 1

A method as provided herein was used to amplify a target nucleic acid. Reactions were prepared to assay for a target nucleic acid from T102A1, which is a DNA molecule from *Staphylococcus aureus*, subspecies SSCmcc. T102A1 has the sequence 5'

```
                                            (SEQ ID NO: 2)
CAACTAATGAAACAGAAAGTCGTAACTATCCTCTAGAAAAAGCGACTTCA

CATCTATTAGGTTATGTTGGTCCCATTAACTCTGAAGAATTAAAACAAAA

AGAATATAAAGGCTATAAAGATGATGCAGTTATTGGTAAAAAGGGACTCG

AAAAACTTTACGATAAAAAGCTCCAACATGAAGATGGCTATCGTGTCACA

ATCGTTGACGATAATAGCAATACAATCGCACATACATTAATAGAGAAAAA

GAAAAAAGATGGCAAAGATATTCAACTAACTATTGATGCTAAAGTTCAAA

AGAGTATTTATAACAACATGAAAAATGATTATGGCTCAGGTACTGCTATC

CACCCTCAAACAGGTGAATTATTAGCACTTGTAAGCACACCTTCATATGA

CGTCTATCCATTTATGTATGCATGAGTAACGAAGAATATAATAAATTAAC

CGAAGATAAAAAAGAACCTCTGCTCAACAAGTTCCAGATTACAACTTCAC

CAGGTTCAACTCAAAAAATATTAACAGCA 3'.

First primer "RLX0513" (nucleotide sequence: 5'
GGCTCAGGTACTGCTATCCACCC 3' (SEQ ID NO: 3))
and second primer "RLX0514"

(nucleotide sequence: 5'
TTTTGAGTTGAACCTGGTGAAGTTG 3' (SEQ ID NO: 4)) were
used to amplify a target sequence from T102A1.
```

Figure 2:
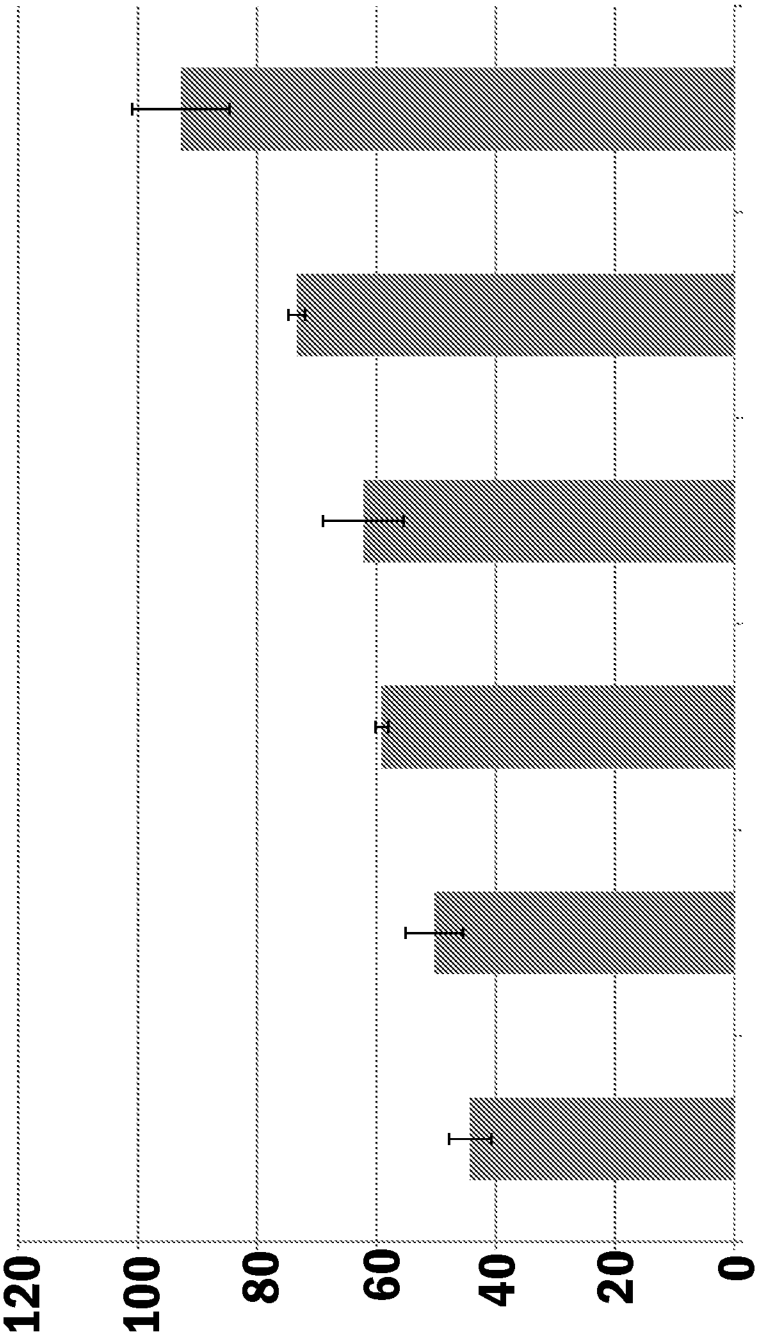
FIG. 2 is a graph depicting results from reactions performed according to a method provided herein.

25 microliter reaction mixtures were prepared, each containing: 50 mM potassium acetate, 20 mM Tris-acetate, pH 7.9, 10 mM magnesium acetate, 1 mM DTT, 0.2 μg/μl bovine serum albumin (BSA), 0.8 M betaine, 1.4 mM each of dATP, dTTP, dGTP, and dCTP, 1 mM rATP, 1×SYTO® 59 (Life Technologies), 1.2 units/μl Bst DNA polymerase (New England BioLabs), 20 units/μl T4 DNA ligase (New England BioLabs), 0.8 μM of first primer RLX0513, 0.8 μM of second primer RLX0514, and 0, 100, 1,000, 10,000, 100,000, or 1,000,000 copies T102A1 template per microliter. The template was preheated at 85 C for 5 minutes and cooled on ice for 5 minutes before addition to the reaction mixture. Upon addition of the template, reaction mixtures were incubated at 42 C for 15 minutes, followed by at 56 C for 90 minutes in a CFX 96 Touch instrument (Bio-Rad). Under these reaction conditions, at 42 C, ligation reactions are relatively favored; at 56 C, polymerase reactions are relatively favored. The inflection points for the assays were determined using a single-threshold method with CFX Manager software (Bio-Rad), and are shown in FIG. 2. The X-axis provides the concentration of template molecules/microliter, and the Y-axis provides the inflection time (in minutes) of the assay. From left to right along the X-axis, the bars are for: 1,000,000, 100,000, 10,000, 1,000, 100, or 0 (no template control/"NTC") copies T102A1 template per microliter As shown in FIG. 2, each of the reactions, including a few as 100 copies template/microliter have inflection times significantly faster than the no template control (NTC) reaction. No template control reactions sometimes show an inflection time; this is due to background non-specific products that are formed over time. The specific inflection times for the reactions are provided below in Table 1. "Cq" refers to the quantification cycle value (time) of the inflection point.

TABLE 1

RLX513/514

| T102A1 | Cq | st. dev |
|---|---|---|
| 10^6 | 44.29 | 3.53 |
| 10^5 | 50.27 | 4.83 |
| 10^4 | 59.11 | 1.07 |
| 10^3 | 62.19 | 6.74 |
| 10^2 | 73.36 | 1.41 |
| NTC | 92.75 | 8.14 |

Example 2

A method as provided herein was used to amplify a target nucleic acid. Reactions were prepared to assay for a target nucleic acid from TH1S3, which is a mRNA molecule from hemagglutinin gene, from influenza A virus, H1N1. TH1 S3 mRNA has the sequence: 5'

(SEQ ID NO: 5)
CGCCGGAUGGCUCUUGGGAAACCGAAGACAGCCACAACGGGAAACUAUGU

AAAUUAAAAGGAAUAGCCCCACUACAAUUGGGGAAAUGUAACAUCGCCGG

AUGGCUCUUGGGAAACCCAGAAUGCGACUCACUGCUUCCAGCGAAAUCAU

-continued

GGUCCUACAUUGUAGAAACACCAAACUCUGAGAAUGGAGCAUGUUAUCCA

GGAGAUUUCAUCGACUAUGAGGAACUGAAGGAGCAAUUGAGCUCAGUAUC

AUCAUUAGAAAGAUUCGAAAUAUUUCCCAAGGAAAGUUCAUGGCCCAACC

ACAACACACUCAAAGGAGUAACAGCAGCAUGCUCCCAUAGGGGAAAAAGC

AGUUUUUACAGAAAUUUGCUAUGGCUGACGAAAACGGGGGACUCAUACCC

AAAGCUGAACAAUUCCUAUGUGAACAAUAAAGGGAAAGAAGUC 3'.

First primer "RLX0585" (nucleotide sequence: 5' CGCCGGATGGCTCTTGGGAAACC 3' (SEQ ID NO: 6)) and second primer "RLX0586"

(nucleotide sequence: 5' TCGCTGGAAGCAGTGAGTCGCATTC 3' (SEQ ID NO: 7)) were used to amplify a target sequence from TH1SC.

Figure 3:
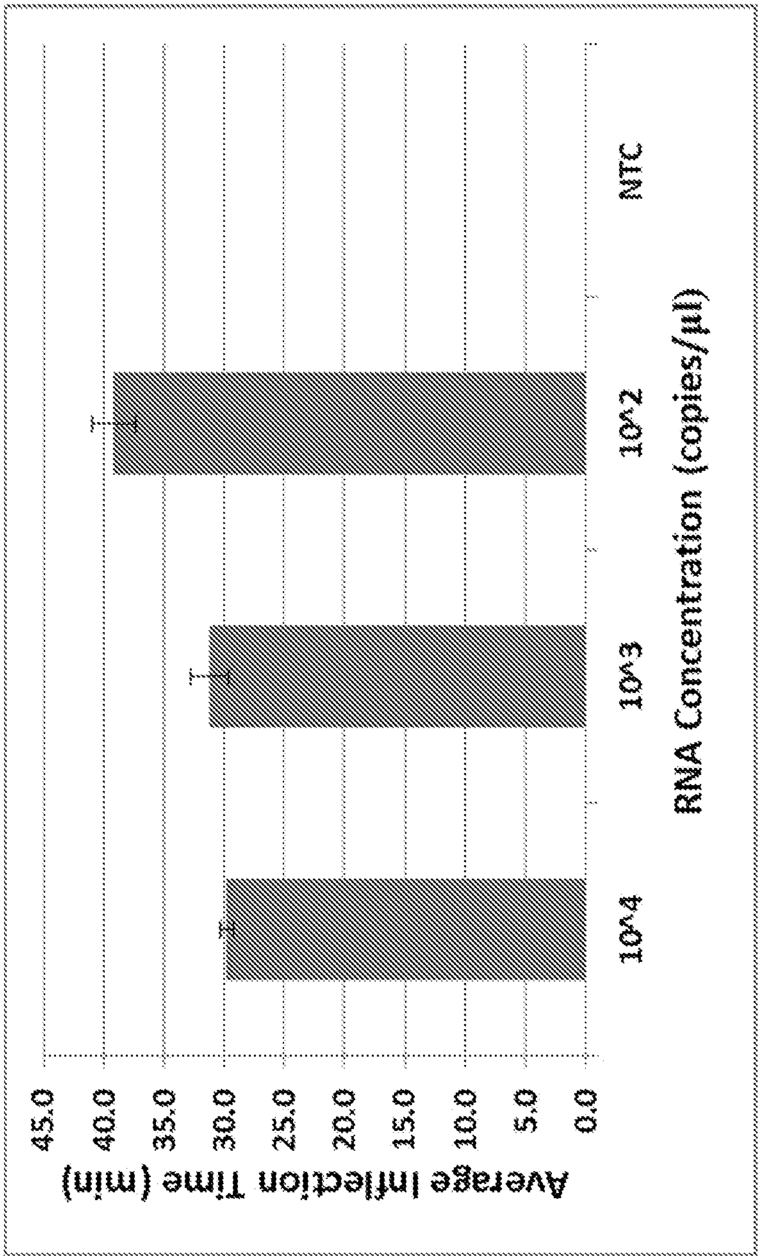
FIG. 3 is a graph depicting results from reactions performed according to a method provided herein.

25 microliter reaction mixtures were prepared, each containing: 50 mM potassium acetate, 20 mM Tris-acetate, pH 7.9, 10 mM magnesium acetate, 1 mM DTT, 0.2 μg/μl bovine serum albumin (BSA), 0.8 M betaine, 1.4 mM each of dATP, dTTP, dGTP, and dCTP, 1 mM rATP, 1×SYTO® 59 (Life Technologies), 1.2 units/μl Bst DNA polymerase (New England BioLabs), 20 units/μl T4 DNA ligase (New England BioLabs), 0.016 units/μl AMV reverse trancriptase enzyme (New England Biolabs), 1 unit/μl murine RNase inhibitor (New England Biolabs), 0.8 μM of first primer RLX0585, 0.8 μM of second primer RLX0586, and 0, 100, 1,000, or 10,000 copies TH1S3 template per microliter. The reaction mixtures were prepared in triplicate for the different quantities of TH1S3 template. The template was preheated at 85 C for 5 minutes and cooled on ice for 5 minutes before addition to the reaction mixture. Upon addition of the template, reaction mixtures were incubated at 42 C for 15 minutes, followed by at 65 C for 90 minutes in a CFX 96 Touch instrument (Bio-Rad). Under these reaction conditions, at 42 C, ligation reactions are relatively favored; at 65 C, polymerase reactions are relatively favored. The inflection points for the assays were determined using a single-threshold method with CFX Manager software (Bio-Rad), and are shown in FIG. 3. The X-axis provides the concentration of template molecules/microliter, and the Y-axis provides the inflection time (in minutes) of the assay. As shown in FIG. 3, each of the template-containing reactions has an inflection time under 40 minutes.

Example 3

A method as provided herein was used to amplify a target nucleic acid. Reactions were prepared to assay for a target nucleic acid from T129A1, which is a mRNA molecule from hemagglutinin gene, HA1 domain (segment 4), from influenza B virus. T129A1 mRNA has the sequence: 5'

(SEQ ID NO: 8)
CUUCUUGAAUUUGAUGUCUAAGAGUAAUUUGCCAACGUGAGGCCAUCAGA

AAGUAUGGUGCGCAAGUGGCAGGAGCAAGGUAAUAAAAGGGUCCUUGCCU

UUAAUUGGUGAAGCAGAUUGCCUCCACGAAAAAUACGGUGGAUUAAACAA

AAGCAAGCCUUACUACACAGGAGAACAUGCAAAAGCCAUAGGAAAUUGCC

CAAUAUGGGUGAAAACACCCUUGAAGCUGGCCAAUGGAACCAAAUAUAGA

-continued

CCGCCUGCAAAACUAUUAAAGGAAAGAGGUUUCUUCGGAAGCGACAGACA

GUAACACUCAACUCUCGACCAUCUGGUGUAACAACCUCG 3'.

First primer "RLX0479" (nucleotide sequence: 5' CGGTGGATTAAACAAAAGCAAGCC 3' (SEQ ID NO: 9)) and second primer "RLX0480"

(nucleotide sequence: 5' ATTGGCCAGCTTCAAGGGTG 3' (SEQ ID NO: 10)) were used to amplify a target sequence from T129A1.

Figure 4:
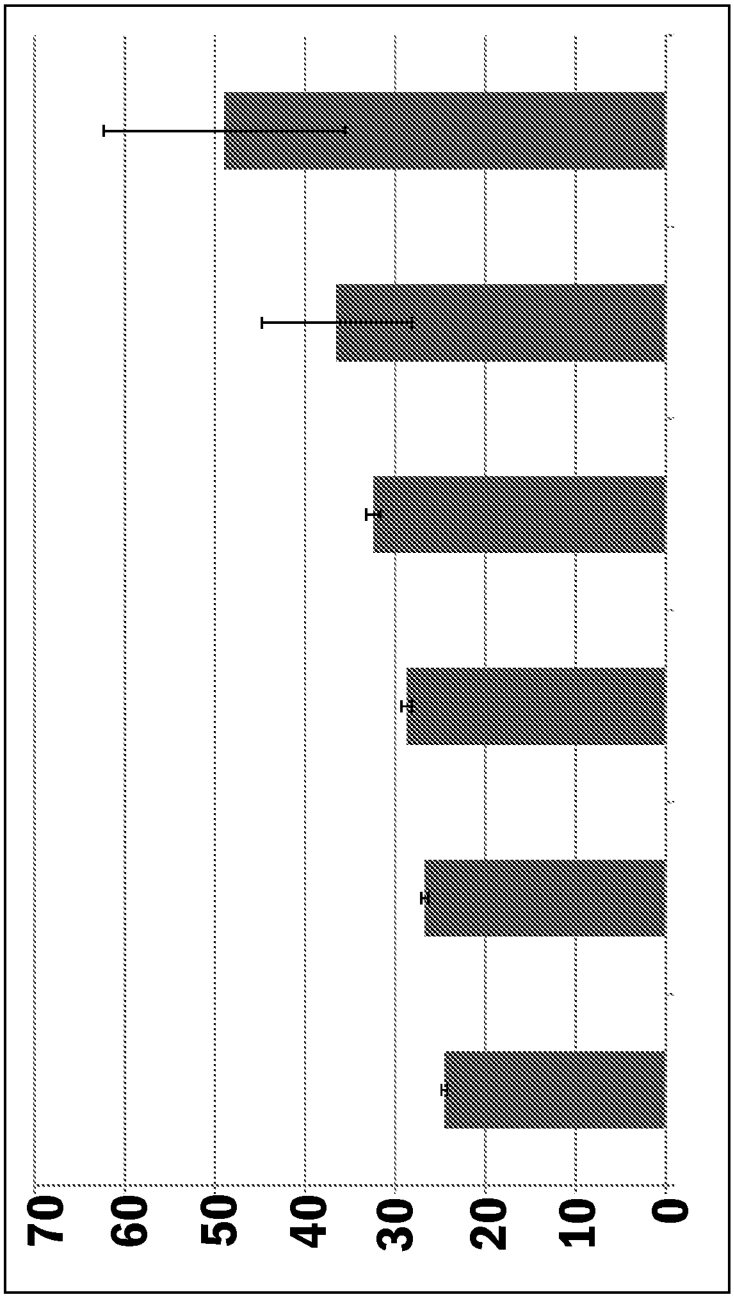
FIG. 4 is a graph depicting results from reactions performed according to a method provided herein.

25 microliter reaction mixtures were prepared, each containing: 50 mM potassium acetate, 20 mM Tris-acetate, pH 7.9, 10 mM magnesium acetate, 1 mM DTT, 0.2 μg/μl bovine serum albumin (BSA), 0.8 M betaine, 1.4 mM each of dATP, dTTP, dGTP, and dCTP, 1 mM rATP, 1×SYTO® 59 (Life Technologies), 1.2 units/μl Bst DNA polymerase (New England BioLabs), 20 units/μl T4 DNA ligase (New England BioLabs), 0.016 units/μl AMV reverse trancriptase enzyme (New England Biolabs), 1 unit/μl murine RNase inhibitor (New England Biolabs), 0.8 μM of first primer RLX0479, 0.8 μM of second primer RLX0480, and 0, 100, 1,000, 10,000, 100,000, or 1,000,000 copies T129A1 template per microliter. Six replicates of the reaction mixture was prepared for each of the different quantities of T129A1 template. The template was preheated at 85 C for 5 minutes and cooled on ice for 5 minutes before addition to the reaction mixture. Upon addition of the template, reaction mixtures were incubated at 42 C for 15 minutes, followed by at 65 C for 90 minutes in a CFX 96 Touch instrument (Bio-Rad). Under these reaction conditions, at 42 C, ligation reactions are relatively favored; at 65 C, polymerase reactions are relatively favored. The inflection points for the assays were determined using a single-threshold method with CFX Manager software (Bio-Rad), and are shown in FIG. 4. The X-axis provides the concentration of template molecules/microliter, and the Y-axis provides the inflection time (in minutes) of the assay. From left to right along the X-axis, the bars are for: 1,000,000, 100,000, 10,000, 1,000, 100, or 0 (no template control/"NTC") copies T129A1 template per microliter. As shown in FIG. 4, each of the template-containing reactions has an inflection time under 40 minutes and significantly faster than the no template control (NTC) reaction.

Nucleotide and amino acid sequences provided herein are artificial sequences, unless otherwise noted.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not. It should also be understood that while the invention provided herein has been described herein using a limited number of terms and phrases for purposes of expediency, the invention could also be described using other terms and phrases not provided herein which also accurately describe the invention. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. As used in the description herein and through the claims that follow, a first object described as containing "at least a portion" of a second object may contain the full amount of/the complete second object. As used in the description herein and throughout the claims that follow, the terms "comprise", "include", and "contain" and related tenses are inclusive and open-ended, and do not exclude additional, unrecited elements or method steps. Also, the presence of broadening words and phrases such as "one or more," "at least," "but not limited to" or other like phrases in some instances shall not be read to mean that the narrower case is intended or required in instances where such broadening phrases may be absent. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

This document contains material subject to copyright protection. The copyright owner (Applicant herein) has no objection to facsimile reproduction by anyone of the patent documents or the patent disclosure, as they appear in the US Patent and Trademark Office patent file or records, but otherwise reserves all copyright rights whatsoever. The following notice shall apply: Copyright 2013-14, Theranos, Inc.

SEQUENCE LISTING

SEQ ID NO 1:
MGHHHHHHHHHHSSGHIEGRASADGPYLQILEQPKQRGFRFRYVCEGPSHGGLPGASSEKNKKSYPQVKICNYV
GPAKVIVQLVTNGKNIHLHAHSLVGICHCEDGICTVTAGPKDMVVGFANLGILHVTKKKVFETLEARMTEACIR
GYNPGLLVHPDLAYLQAEGGGDRQLGDREKELIRQAALQQTKEMDLSVVRLMFTAFLPDSTGSFTRRLEPVVSD
AIYDSKAPNASNLKIVRMDRTAGCVTGGEEIYLLCDKVQKDDIQIRFYEEEENGGVWEGFGDFSPTDVHRQFAI
VFKTPKYKDINITKPASVFVQLRRKSDLETSEPKPFLYYPEIKDKEEVQRKRQKGSSGTSGGGSGGGMTLEEAR
KRVNELRDLIRYHNYRYYVLADPEISDAEYDRLLRELKELEERFPELKSPDSPTLQVGARPLEATFRPVRHPTR
MYSLDNAFNLDELKAFEERIERALGRKGPFAYTVEHKVDGLSVNLYYEEGVLVYGATRGDGEVGEEVTQNLLTI
PTIPRRLKGVPERLEVRGEVYMPIEAFLRLNEELEERGERIFKNPRNAAAGSLRQKDPRITAKRGLRATFYALG
LGLEEVEREGVATQFALLHWLKEKGFPVEHGYARAVGAEGVEAVYQDWLKKRRALPFEADGVVVKLDELALWRE
LGYTARAPRFAIAYKFPAEEKETRLLDVVFQVGRTGRVTPVGILEPVFLEGSEVSRVTLHNESYIEELDIRIGD
WVLVHKAGGVIPEVLRVLKERRTGEERPIRWPETCPECGHRLLKEGKVHRCPNPLCPAKRFEAIRHFASRKAMD
IQGLGEKLIERLLEKGLVKDVADLYRLRKEDLVGLERMGEKSAQNLLRQWESKKRGLERLLYALGLPGVGEVLA
RNLAARFGNMDRLLEASLEELLEVEEVGELTARAILETLKDPAFRDLVRRLKEAGVEMEAKEKGGEALKGLTFV
ITGELSRPREEVICALLRRLGAKVTDSVSRKTSYLVVGENPGSKLEKARALGVPTLTEEELYRLLEARTGKKAE
ELV

-continued

SEQUENCE LISTING

SEQ ID NO: 2:
CAACTAATGAAACAGAAAGTCGTAACTATCCTCTAGAAAAAGCGACTTCACATCTATTAGGTTATGTTGGTCCC
ATTAACTCTGAAGAATTAAAACAAAAAGAATATAAAGGCTATAAAGATGATGCAGTTATTGGTAAAAAGGGACT
CGAAAAACTTTACGATAAAAAGCTCCAACATGAAGATGGCTATCGTGTCACAATCGTTGACGATAATAGCAATA
CAATCGCACATACATTAATAGAGAAAAAGAAAAAAGATGGCAAAGATATTCAACTAACTATTGATGCTAAAGTT
CAAAAGAGTATTTATAACAACATGAAAAATGATTATGGCTCAGGTACTGCTATCCACCCTCAAACAGGTGAATT
ATTAGCACTTGTAAGCACACCTTCATATGACGTCTATCCATTTATGTATGCATGAGTAACGAAGAATATAATAA
ATTAACCGAAGATAAAAAAGAACCTCTGCTCAACAAGTTCCAGATTACAACTTCACCAGGTTCAACTCAAAAAA
TATTAACAGCA

SEQ ID NO: 3:
GGCTCAGGTACTGCTATCCACCC

SEQ ID NO: 4:
TTTTGAGTTGAACCTGGTGAAGTTG

SEQ ID NO: 5:
CGCCGGAUGGCUCUUGGGAAACCGAAGACAGCCACAACGGGAAACUAUGUAAAUUAAAAGGAAUAGCCCCACUA
CAAUUGGGGAAAUGUAACAUCGCCGGAUGGCUCUUGGGAAACCCAGAAUGCGACUCACUGCUUCCAGCGAAAUC
AUGGUCCUACAUUGUAGAAACACCAAACUCUGAGAAUGGAGCAUGUUAUCCAGGAGAUUUCAUCGACUAUGAGG
AACUGAAGGAGCAAUUGAGCUCAGUAUCAUCAUUAGAAAGAUUCGAAAUAUUUCCCAAGGAAAGUUCAUGGCCC
AACCACAACACACUCAAAGGAGUAACAGCAGCAUGCUCCCAUAGGGGAAAAAGCAGUUUUUACAGAAAUUUGCU
AUGGCUGACGAAAACGGGGGACUCAUACCCAAAGCUGAACAAUUCCUAUGUGAACAAUAAAGGGAAAGAAGUC

SEQ ID NO: 6:
CGCCGGATGGCTCTTGGGAAACC

SEQ ID NO: 7:
TCGCTGGAAGCAGTGAGTCGCATTC

SEQ ID NO: 8:
CUUCUUGAAUUUGAUGUCUAAGAGUAAUUUGCCAACGUGAGGCCAUCAGAAAGUAUGGUGCGCAAGUGGCAGGA
GCAAGGUAAUAAAAGGGUCCUUGCCUUUAAUUGGUGAAGCAGAUUGCCUCCACGAAAAAUACGGUGGAUUAAAC
AAAAGCAAGCCUUACUACACAGGAGAACAUGCAAAAGCCAUAGGAAAUUGCCCAAUAUGGGUGAAAACACCCUU
GAAGCUGGCCAAUGGAACCAAAUAUAGACCGCCUGCAAAACUAUUAAAGGAAAGAGGUUUCUUCGGAAGCGACA
GACAGUAACACUCAACUCUCGACCAUCUGGUGUAACAACCUCG

SEQ ID NO: 9:
CGGTGGATTAAACAAAAGCAAGCC

SEQ ID NO: 10:
ATTGGCCAGCTTCAAGGGTG

We claim:

1. A method of replicating a double stranded nucleic acid template, the method comprising, incubating in a reaction mixture a first primer, a DNA polymerase, a nucleic acid ligase, a first copy of a single template linear double-stranded nucleic acid, a second copy of the single template linear double-stranded nucleic acid, a third copy of the single template linear double-stranded nucleic acid, a first copy of a multiple template linear double-stranded nucleic acid, and a second copy of the multiple template linear double-stranded nucleic acid for at least 5 minutes at a temperature of no greater than 80° C., wherein:

the DNA polymerase has strand-displacement activity, the nucleic acid ligase has activity on blunt-ends of double-stranded nucleic acids, each copy of the single template linear double-stranded nucleic acids contains a single copy of the double stranded nucleic acid template, each copy of the single template linear double-stranded nucleic acid and multiple template linear double-stranded nucleic acid comprises: i) a first strand and a second strand, each strand comprising a 5' end and a 3' end, and ii) a first end and a second end, the first end comprising the 5' end of the first strand and the 3' end of the second strand, and the second end comprising the 5' end of the second strand and the 3' end of the first strand, and during the incubation of the reaction mixture, i) the first primer anneals to the first strand of the first copy of the single template linear double-stranded nucleic acid and serves as a primer for the generation of an extension product of the first primer, wherein the extension product of the first primer is complementary to the first strand of the single template linear double stranded nucleic acid;

ii) the second end of the second copy of the single template linear double-stranded nucleic acid is ligated to the first end of the third copy of the single template linear double-stranded nucleic acid; and iii) a cross-over structure comprising the second strand of the first copy of the multiple template linear double-stranded nucleic acid annealed to the first strand of the second copy of the multiple template linear double-stranded nucleic acid is formed, wherein the 3' end of the first strand of the second copy multiple template linear double stranded nucleic acid is annealed to the second strand of the first copy multiple template linear double-stranded nucleic acid past the 5' end of the second strand of the first copy multiple template linear double-stranded nucleic acid;

wherein the multiple template linear double-stranded nucleic acid comprises a repeating unit of nucleic acid regions, wherein each of said nucleic acid regions comprises nucleic acid sequences, each of which constitutes a single template.

2. The method of claim 1, wherein the reaction mixture is incubated at a first temperature and a second temperature, wherein during incubation at the first temperature, the first copy of a single template linear double-stranded nucleic acid undergoes a ligation reaction by the nucleic acid ligase to produce a second double-stranded nucleic acid, and during incubation at the second temperature, the first copy of a single template linear double-stranded nucleic acid and/or the second double-stranded nucleic acid undergoes a polymerase reaction by the isolated nucleic acid polymerase, and wherein the first temperature and the second temperature are no greater than about 70° C.

3. The method of claim 2, wherein the ligation reaction is an end-to-end ligation reaction.

4. The method of claim 2, wherein the polymerase reaction is a primer-based replication reaction and/or a cross-over strand replication reaction.

5. The method of claim 2, wherein the second double-stranded nucleic acid comprises at least two copies of the first copy of a single template linear double-stranded nucleic acid.

6. The method of claim 2, wherein the first temperature and second temperature are different.

7. The method of claim 2, wherein the first temperature is about 42° C.

8. The method of claim 2, wherein the second temperature is about 56° C.

9. The method of claim 2, wherein the second temperature is about 65° C.

10. The method of claim 2, wherein the first temperature and second temperature are the same.

11. A method of replicating a double stranded nucleic acid template, the method comprising, incubating in a reaction mixture a first primer, a DNA polymerase, a nucleic acid ligase, a first copy of a single template linear double-stranded nucleic acid, a second copy of the single template linear double-stranded nucleic acid, a third copy of the single template linear double-stranded nucleic acid, a first copy of a multiple template linear double-stranded nucleic acid, and a second copy of the multiple template linear double-stranded nucleic acid for at least 5 minutes at a temperature of no greater than 80° C., wherein:

the DNA polymerase has strand-displacement activity, the nucleic acid ligase has activity on blunt-ends of double-stranded nucleic acids, each copy of the single template linear double-stranded nucleic acids contains a single copy of the double stranded nucleic acid template, each copy of the single template linear double-stranded nucleic acid and multiple template linear double-stranded nucleic acid comprises: i) a first strand and a second strand, each strand comprising a 5' end and a 3' end, and ii) a first end and a second end, the first end comprising the 5' end of the first strand and the 3' end of the second strand, and the second end comprising the 5' end of the second strand and the 3' end of the first strand, and during the incubation of the reaction mixture, i) the first primer anneals to the first strand of the first copy of the single template linear double-stranded nucleic acid and serves as a primer for the generation of an extension product of the first primer, wherein the extension product of the first primer is complementary to the first strand of the single template linear double stranded nucleic acid;

ii) the second end of the second copy of the single template linear double-stranded nucleic acid is ligated to the first end of the third copy of the single template linear double-stranded nucleic acid; and iii) a cross-over structure comprising the second strand of the first copy of the multiple template linear double-stranded nucleic acid annealed to the first strand of the second copy of the multiple template linear double-stranded nucleic acid is formed, wherein the 3' end of the first strand of the second copy multiple template linear double stranded nucleic acid is annealed to the second strand of the first copy multiple template linear double-stranded nucleic acid past the 5' end of the second strand of the first copy multiple template linear double-stranded nucleic acid;

wherein the multiple template linear double-stranded nucleic acid comprises a repeating unit of nucleic acid regions, wherein each of said nucleic acid regions comprises nucleic acid sequences, each of which constitutes a single template;

wherein the reaction mixture comprises a second primer, wherein the second primer is complementary to the second strand of the first copy of the single template linear double-stranded nucleic acid.

12. A method of replicating a double stranded nucleic acid template, the method comprising, incubating in a reaction mixture a first primer, a DNA polymerase, a nucleic acid ligase, a first copy of a single template linear double-stranded nucleic acid, a second copy of the single template linear double-stranded nucleic acid, a third copy of the single template linear double-stranded nucleic acid, a first copy of a multiple template linear double-stranded nucleic acid, and a second copy of the multiple template linear double-stranded nucleic acid for at least 5 minutes at a temperature of no greater than 80° C., wherein:

the DNA polymerase has strand-displacement activity, the nucleic acid ligase has activity on blunt-ends of double-stranded nucleic acids, each copy of the single template linear double-stranded nucleic acids contains a single copy of the double stranded nucleic acid template, each copy of the single template linear double-stranded nucleic acid and multiple template linear double-stranded nucleic acid comprises: i) a first strand and a second strand, each strand comprising a 5' end and a 3' end, and ii) a first end and a second end, the first end comprising the 5' end of the first strand and the 3' end of the second strand, and the second end comprising the 5' end of the second strand and the 3' end of the first strand, and during the incubation of the reaction mixture, i) the first primer anneals to the first strand of the first copy of the single template linear double-stranded nucleic acid and serves as a primer for the generation of an extension product of the first primer, wherein the extension product of the first primer is complementary to the first strand of the single template linear double stranded nucleic acid;

ii) the second end of the second copy of the single template linear double-stranded nucleic acid is ligated to the first end of the third copy of the single template linear double-stranded nucleic acid; and iii) a cross-over structure comprising the second strand of the first copy of the multiple template linear double-stranded nucleic acid annealed to the first strand of the second copy of the multiple template linear double-stranded nucleic acid is formed, wherein the 3' end of the first strand of the second copy multiple template linear double stranded nucleic acid is annealed to the second strand of the first copy multiple template linear double-stranded nucleic acid past the 5' end of the second strand of the first copy multiple template linear double-stranded nucleic acid;

wherein the multiple template linear double-stranded nucleic acid comprises a repeating unit of nucleic acid regions, wherein each of said nucleic acid regions comprises nucleic acid sequences, each of which constitutes a single template;

wherein the reaction mixture further comprises a reverse transcriptase.

13. The method of claim 12, further comprising providing a single-stranded RNA and reverse transcribing said single-stranded RNA and producing the first single template linear double-stranded nucleic acid.

* * * * *

SEQUENCE LISTING

<160> NUMBER OF SEQ ID NOS: 11

<210> SEQ ID NO 1
<211> LENGTH: 1038
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Gly His His His His His His His His His His Ser Ser Gly His
1               5                   10                  15

Ile Glu Gly Arg Ala Ser Ala Asp Gly Pro Tyr Leu Gln Ile Leu Glu
            20                  25                  30

Gln Pro Lys Gln Arg Gly Phe Arg Phe Arg Tyr Val Cys Glu Gly Pro
        35                  40                  45

Ser His Gly Gly Leu Pro Gly Ala Ser Ser Glu Lys Asn Lys Lys Ser
    50                  55                  60

Tyr Pro Gln Val Lys Ile Cys Asn Tyr Val Gly Pro Ala Lys Val Ile
65                  70                  75                  80

-continued

```
Val Gln Leu Val Thr Asn Gly Lys Asn Ile His Leu His Ala His Ser
                85                  90                  95

Leu Val Gly Lys His Cys Glu Asp Gly Ile Cys Thr Val Thr Ala Gly
            100                 105                 110

Pro Lys Asp Met Val Val Gly Phe Ala Asn Leu Gly Ile Leu His Val
        115                 120                 125

Thr Lys Lys Lys Val Phe Glu Thr Leu Glu Ala Arg Met Thr Glu Ala
    130                 135                 140

Cys Ile Arg Gly Tyr Asn Pro Gly Leu Leu Val His Pro Asp Leu Ala
145                 150                 155                 160

Tyr Leu Gln Ala Glu Gly Gly Gly Asp Arg Gln Leu Gly Asp Arg Glu
                165                 170                 175

Lys Glu Leu Ile Arg Gln Ala Ala Leu Gln Gln Thr Lys Glu Met Asp
            180                 185                 190

Leu Ser Val Val Arg Leu Met Phe Thr Ala Phe Leu Pro Asp Ser Thr
        195                 200                 205

Gly Ser Phe Thr Arg Arg Leu Glu Pro Val Val Ser Asp Ala Ile Tyr
    210                 215                 220

Asp Ser Lys Ala Pro Asn Ala Ser Asn Leu Lys Ile Val Arg Met Asp
225                 230                 235                 240

Arg Thr Ala Gly Cys Val Thr Gly Gly Glu Glu Ile Tyr Leu Leu Cys
                245                 250                 255

Asp Lys Val Gln Lys Asp Asp Ile Gln Ile Arg Phe Tyr Glu Glu Glu
            260                 265                 270

Glu Asn Gly Gly Val Trp Glu Gly Phe Gly Asp Phe Ser Pro Thr Asp
        275                 280                 285

Val His Arg Gln Phe Ala Ile Val Phe Lys Thr Pro Lys Tyr Lys Asp
    290                 295                 300

Ile Asn Ile Thr Lys Pro Ala Ser Val Phe Val Gln Leu Arg Arg Lys
305                 310                 315                 320

Ser Asp Leu Glu Thr Ser Glu Pro Lys Pro Phe Leu Tyr Tyr Pro Glu
                325                 330                 335

Ile Lys Asp Lys Glu Glu Val Gln Arg Lys Arg Gln Lys Gly Ser Ser
            340                 345                 350

Gly Thr Ser Gly Gly Gly Ser Gly Gly Gly Met Thr Leu Glu Glu Ala
        355                 360                 365

Arg Lys Arg Val Asn Glu Leu Arg Asp Leu Ile Arg Tyr His Asn Tyr
    370                 375                 380

Arg Tyr Tyr Val Leu Ala Asp Pro Glu Ile Ser Asp Ala Glu Tyr Asp
385                 390                 395                 400

Arg Leu Leu Arg Glu Leu Lys Glu Leu Glu Glu Arg Phe Pro Glu Leu
                405                 410                 415

Lys Ser Pro Asp Ser Pro Thr Leu Gln Val Gly Ala Arg Pro Leu Glu
            420                 425                 430

Ala Thr Phe Arg Pro Val Arg His Pro Thr Arg Met Tyr Ser Leu Asp
        435                 440                 445

Asn Ala Phe Asn Leu Asp Glu Leu Lys Ala Phe Glu Glu Arg Ile Glu
    450                 455                 460

Arg Ala Leu Gly Arg Lys Gly Pro Phe Ala Tyr Thr Val Glu His Lys
465                 470                 475                 480

Val Asp Gly Leu Ser Val Asn Leu Tyr Tyr Glu Glu Gly Val Leu Val
                485                 490                 495

Tyr Gly Ala Thr Arg Gly Asp Gly Glu Val Gly Glu Glu Val Thr Gln
```

-continued

```
            500                 505                 510

Asn Leu Leu Thr Ile Pro Thr Ile Pro Arg Arg Leu Lys Gly Val Pro
        515                 520                 525

Glu Arg Leu Glu Val Arg Gly Glu Val Tyr Met Pro Ile Glu Ala Phe
    530                 535                 540

Leu Arg Leu Asn Glu Glu Leu Glu Glu Arg Gly Glu Arg Ile Phe Lys
545                 550                 555                 560

Asn Pro Arg Asn Ala Ala Ala Gly Ser Leu Arg Gln Lys Asp Pro Arg
                565                 570                 575

Ile Thr Ala Lys Arg Gly Leu Arg Ala Thr Phe Tyr Ala Leu Gly Leu
            580                 585                 590

Gly Leu Glu Glu Val Glu Arg Glu Gly Val Ala Thr Gln Phe Ala Leu
        595                 600                 605

Leu His Trp Leu Lys Glu Lys Gly Phe Pro Val Glu His Gly Tyr Ala
    610                 615                 620

Arg Ala Val Gly Ala Glu Gly Val Glu Ala Val Tyr Gln Asp Trp Leu
625                 630                 635                 640

Lys Lys Arg Arg Ala Leu Pro Phe Glu Ala Asp Gly Val Val Val Lys
                645                 650                 655

Leu Asp Glu Leu Ala Leu Trp Arg Glu Leu Gly Tyr Thr Ala Arg Ala
            660                 665                 670

Pro Arg Phe Ala Ile Ala Tyr Lys Phe Pro Ala Glu Glu Lys Glu Thr
        675                 680                 685

Arg Leu Leu Asp Val Val Phe Gln Val Gly Arg Thr Gly Arg Val Thr
    690                 695                 700

Pro Val Gly Ile Leu Glu Pro Val Phe Leu Glu Gly Ser Glu Val Ser
705                 710                 715                 720

Arg Val Thr Leu His Asn Glu Ser Tyr Ile Glu Glu Leu Asp Ile Arg
                725                 730                 735

Ile Gly Asp Trp Val Leu Val His Lys Ala Gly Gly Val Ile Pro Glu
            740                 745                 750

Val Leu Arg Val Leu Lys Glu Arg Arg Thr Gly Glu Glu Arg Pro Ile
        755                 760                 765

Arg Trp Pro Glu Thr Cys Pro Glu Cys Gly His Arg Leu Leu Lys Glu
    770                 775                 780

Gly Lys Val His Arg Cys Pro Asn Pro Leu Cys Pro Ala Lys Arg Phe
785                 790                 795                 800

Glu Ala Ile Arg His Phe Ala Ser Arg Lys Ala Met Asp Ile Gln Gly
                805                 810                 815

Leu Gly Glu Lys Leu Ile Glu Arg Leu Leu Glu Lys Gly Leu Val Lys
            820                 825                 830

Asp Val Ala Asp Leu Tyr Arg Leu Arg Lys Glu Asp Leu Val Gly Leu
        835                 840                 845

Glu Arg Met Gly Glu Lys Ser Ala Gln Asn Leu Leu Arg Gln Ile Glu
    850                 855                 860

Glu Ser Lys Lys Arg Gly Leu Glu Arg Leu Leu Tyr Ala Leu Gly Leu
865                 870                 875                 880

Pro Gly Val Gly Glu Val Leu Ala Arg Asn Leu Ala Ala Arg Phe Gly
                885                 890                 895

Asn Met Asp Arg Leu Leu Glu Ala Ser Leu Glu Glu Leu Leu Glu Val
            900                 905                 910

Glu Glu Val Gly Glu Leu Thr Ala Arg Ala Ile Leu Glu Thr Leu Lys
        915                 920                 925
```

-continued

```
Asp Pro Ala Phe Arg Asp Leu Val Arg Arg Leu Lys Glu Ala Gly Val
    930                 935                 940

Glu Met Glu Ala Lys Glu Lys Gly Gly Glu Ala Leu Lys Gly Leu Thr
945                 950                 955                 960

Phe Val Ile Thr Gly Glu Leu Ser Arg Pro Arg Glu Glu Val Lys Ala
                965                 970                 975

Leu Leu Arg Arg Leu Gly Ala Lys Val Thr Asp Ser Val Ser Arg Lys
            980                 985                 990

Thr Ser Tyr Leu Val Val Gly Glu  Asn Pro Gly Ser Lys  Leu Glu Lys
        995                 1000                 1005

Ala Arg  Ala Leu Gly Val Pro  Thr Leu Thr Glu Glu  Glu Leu Tyr
    1010                 1015                 1020

Arg Leu  Leu Glu Ala Arg Thr  Gly Lys Lys Ala Glu  Glu Leu Val
    1025                 1030                 1035


<210> SEQ ID NO 2
<211> LENGTH: 529
<212> TYPE: DNA
<213> ORGANISM: Staphylococcus aureus
<220> FEATURE:
<223> OTHER INFORMATION: Subspecies SSCmec

<400> SEQUENCE: 2

caactaatga aacagaaagt cgtaactatc ctctagaaaa agcgacttca catctattag      60

gttatgttgg tcccattaac tctgaagaat taaaacaaaa agaatataaa ggctataaag     120

atgatgcagt tattggtaaa aagggactcg aaaaacttta cgataaaaag ctccaacatg     180

aagatggcta tcgtgtcaca atcgttgacg ataatagcaa tacaatcgca catacattaa     240

tagagaaaaa gaaaaaagat ggcaaagata ttcaactaac tattgatgct aaagttcaaa     300

agagtattta taacaacatg aaaaatgatt atggctcagg tactgctatc caccctcaaa     360

caggtgaatt attagcactt gtaagcacac cttcatatga cgtctatcca tttatgtatg     420

catgagtaac gaagaatata ataaattaac cgaagataaa aaagaacctc tgctcaacaa     480

gttccagatt acaacttcac caggttcaac tcaaaaaata ttaacagca                 529


<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

ggctcaggta ctgctatcca ccc                                               23


<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

ttttgagttg aacctggtga agttg                                             25


<210> SEQ ID NO 5
<211> LENGTH: 443
```

-continued

```
<212> TYPE: RNA
<213> ORGANISM: Influenza A virus

<400> SEQUENCE: 5

cgccggaugg cucuugggaa accgaagaca gccacaacgg gaaacuaugu aaauuaaaag     60

gaauagcccc acuacaauug gggaaaugua acaucgccgg auggcucuug ggaaacccag    120

aaugcgacuc acugcuucca gcgaaaucau gguccuacau uguagaaaca ccaaacucug    180

agaauggagc auguuaucca ggagauuuca ucgacuauga ggaacugaag gagcaauuga    240

gcucaguauc aucauuagaa agauucgaaa uauuucccaa ggaaaguuca uggcccaacc    300

acaacacacu caaaggagua acagcagcau gcucccauag gggaaaaagc aguuuuuaca    360

gaaauuugcu auggcugacg aaaacggggg acucauaccc aaagcugaac aauuccuaug    420

ugaacaauaa agggaaagaa guc                                            443


<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

cgccggatgg ctcttgggaa acc                                             23


<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

tcgctggaag cagtgagtcg cattc                                           25


<210> SEQ ID NO 8
<211> LENGTH: 339
<212> TYPE: RNA
<213> ORGANISM: Influenza B virus

<400> SEQUENCE: 8

cuucuugaau uugaugucua agaguaauuu gccaacguga ggccaucaga aaguauggug     60

cgcaaguggc aggagcaagg uaauaaaagg guccuugccu uuaauuggug aagcagauug    120

ccuccacgaa aaauacggug gauuaaacaa aagcaagccu uacuacacag gagaacaugc    180

aaaagccaua ggaaauugcc caauaugggu gaaaacaccc uugaagcugg ccaauggaac    240

caaauauaga ccgccugcaa aacuauuaaa ggaaagaggu uucuucggaa gcgacagaca    300

guaacacuca acucucgacc aucuggugua acaaccucg                          339


<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

cggtggatta aacaaaagca agcc                                            24
```

-continued

```
<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

attggccagc ttcaagggtg                                                20


<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 11

His His His His His His His His His His
1               5                   10
```